United States Patent
Wheeler et al.

(10) Patent No.: US 9,249,443 B2
(45) Date of Patent: *Feb. 2, 2016

(54) CELL CULTURE AND CELL ASSAYS USING DIGITAL MICROFLUIDICS

(75) Inventors: Aaron R. Wheeler, Toronto (CA); Irena Barbulovic-Nad, Toronto (CA)

(73) Assignee: The Governing Council of the University of Toronto (CA)

( * ) Notice: Subject to any disclaimer, the term of this patent is extended or adjusted under 35 U.S.C. 154(b) by 462 days.

This patent is subject to a terminal disclaimer.

(21) Appl. No.: 12/867,108

(22) PCT Filed: Nov. 20, 2008

(86) PCT No.: PCT/CA2008/002040
§ 371 (c)(1),
(2), (4) Date: Aug. 11, 2010

(87) PCT Pub. No.: WO2009/100516
PCT Pub. Date: Aug. 20, 2009

(65) Prior Publication Data
US 2010/0311599 A1 Dec. 9, 2010

Related U.S. Application Data

(63) Continuation-in-part of application No. 12/285,020, filed on Sep. 26, 2008, now Pat. No. 8,367,370.

(60) Provisional application No. 61/064,002, filed on Feb. 11, 2008.

(51) Int. Cl.
*C12Q 1/02* (2006.01)
*C12N 5/02* (2006.01)
(Continued)

(52) U.S. Cl.
CPC .............. *C12Q 1/02* (2013.01); *B01F 13/0071* (2013.01); *B01F 13/0076* (2013.01);
(Continued)

(58) Field of Classification Search
CPC ... B01F 13/0071; B01F 13/0076; C12Q 1/02; B01L 3/502792; B01L 22/027; B01L 22/0605; B01L 2300/0819; B01L 2300/0867; B01L 2300/089; B01L 2400/0427; B01L 2400/0688; C12M 23/16; C12M 25/01; C12M 25/08; C12M 33/00; C12M 41/00; G01N 33/54386
USPC .............. 435/7.2, 29, 287.1, 288.7; 506/7, 36
See application file for complete search history.

(56) References Cited

U.S. PATENT DOCUMENTS

| 4,569,575 A | 2/1986 | Le Pesant et al. |
| 4,636,785 A | 1/1987 | Le Pesant |

(Continued)

FOREIGN PATENT DOCUMENTS

| WO | 03045556 A2 | 6/2003 |
| WO | 2003045556 A3 | 6/2003 |

(Continued)

OTHER PUBLICATIONS

Moon, H., et al. "An integrated digital microfluidic chip for multiplexed proteomic sample preparation and analysis by MALDI-MS." Lab on a Chip, Sep. 2006; vol. 6(9), 1213-1219. ISSN: 1473-0197. p. 1213-1219.

(Continued)

*Primary Examiner* — Michael Hobbs
(74) *Attorney, Agent, or Firm* — Bacon & Thomas, PLLC

(57) ABSTRACT

Devices and methods for implementing cell-based assays and long-term cell culture. The device and method are based on digital microfluidics (DMF) which is used to actuate nanoliter droplets of reagents and cells on a planar array of electrodes. DMF method is suitable for assaying and culturing both cells in suspension and cells grown on surface (adherent cells). This method is advantageous for cell culture and assays due to the automated manipulation of multiple reagents in addition to reduced reagent use and analysis time. No adverse effects of actuation by DMF were observed in assays for cell viability, proliferation, and biochemistry. These results suggest that DMF has great potential as a simple yet versatile analytical tool for implementing cell-based assays and cell culture on the microscale.

77 Claims, 12 Drawing Sheets

(51) Int. Cl.
  *B01F 13/00* (2006.01)
  *B01L 3/00* (2006.01)
  *C12M 3/06* (2006.01)
  *C12M 1/12* (2006.01)
  *C12M 1/26* (2006.01)
  *C12M 1/34* (2006.01)
  *G01N 33/543* (2006.01)

(52) U.S. Cl.
  CPC ......... *B01L 3/502792* (2013.01); *C12M 23/16* (2013.01); *C12M 25/01* (2013.01); *C12M 25/08* (2013.01); *C12M 33/00* (2013.01); *C12M 41/00* (2013.01); *G01N 33/54386* (2013.01); *B01L 2200/027* (2013.01); *B01L 2200/0605* (2013.01); *B01L 2300/089* (2013.01); *B01L 2300/0819* (2013.01); *B01L 2300/0867* (2013.01); *B01L 2400/0427* (2013.01); *B01L 2400/0688* (2013.01)

(56) References Cited

U.S. PATENT DOCUMENTS

| | | | |
|---|---|---|---|
| 4,818,052 | A | 4/1989 | Le Pesant et al. |
| 5,486,337 | A | 1/1996 | Ohkawa |
| 6,352,838 | B1 | 3/2002 | Krulevitch et al. |
| 6,565,727 | B1 | 5/2003 | Shenderov |
| 6,773,566 | B2 | 8/2004 | Shenderov |
| 6,911,132 | B2 | 6/2005 | Pamula et al. |
| 6,989,234 | B2 | 1/2006 | Kolar et al. |
| 7,147,763 | B2 | 12/2006 | Elrod et al. |
| 7,163,612 | B2 | 1/2007 | Sterling et al. |
| 7,214,302 | B1 | 5/2007 | Reihs et al. |
| 7,255,780 | B2 | 8/2007 | Shenderov |
| 7,328,979 | B2 | 2/2008 | Decre et al. |
| 7,329,545 | B2 | 2/2008 | Pamula et al. |
| 2002/0150683 | A1* | 10/2002 | Troian et al. ............ 427/256 |
| 2004/0055536 | A1* | 3/2004 | Kolar et al. ............ 118/626 |
| 2004/0058450 | A1* | 3/2004 | Pamula et al. ............ 436/150 |
| 2004/0171169 | A1 | 9/2004 | Kallury et al. |
| 2004/0211659 | A1 | 10/2004 | Velev |
| 2005/0115836 | A1 | 6/2005 | Reihs |
| 2005/0148091 | A1 | 7/2005 | Kitaguchi et al. |
| 2005/0191759 | A1 | 9/2005 | Pedersen-Bjergaard et al. |
| 2007/0023292 | A1 | 2/2007 | Kim et al. |
| 2007/0037225 | A1* | 2/2007 | Metzger et al. ............ 435/7.22 |
| 2007/0148763 | A1 | 6/2007 | Huh et al. |
| 2007/0242111 | A1 | 10/2007 | Pamula et al. |
| 2008/0044914 | A1 | 2/2008 | Pamula et al. |
| 2008/0156983 | A1 | 7/2008 | Fourrier et al. |
| 2008/0185339 | A1 | 8/2008 | Delapierre et al. |
| 2008/0281471 | A1 | 11/2008 | Smith et al. |
| 2009/0203063 | A1 | 8/2009 | Wheeler et al. |

FOREIGN PATENT DOCUMENTS

| | | |
|---|---|---|
| WO | 2005118129 A1 | 12/2005 |
| WO | WO 2007/120241 A2 | 10/2007 |
| WO | 2007136386 A2 | 11/2007 |
| WO | WO 2008/051310 A3 | 5/2008 |
| WO | 2009111723 A1 | 9/2009 |
| WO | 2009111723 A9 | 11/2009 |

OTHER PUBLICATIONS

Wheeler, A., et al, "Electrowetting-based microfluidics for analysis of peptides and proteins by matrix-assisted laser desorption/ionization mass spectrometry" Analytical Chemistry. Aug. 15, 2004; vol. 76 (16), 4833-4838. ISSN: 0003-2700.

Chatterjee, D., et al. "Droplet-based microfluidics with nonaqueous solvents and solutions," Lab on a Chip, Feb. 2006; vol. 6 (2); 199-206. ISSN: 1473-0197.

Link, D., et al. "Electric control of droplets in microfluidic devices." Angewandte Chemie (International edition in English). Apr. 10, 2006; vol. 45 (16), 2556-2560, ISSN: 1433-7851.

Verkman, A.S. "Drug Discovery in Academia" American Journal Physiology Cell Physiology, 286:465-474, 2004.

El-Ali, Jamil, et al. "Cells on chips." Nature Publishing Group: vol. 442, Jul. 27, 2006. pp. 403-411.

Unger, Marc A., et al. "Monolithic Microfabricated Valves and Pumps by Multilayer Soft Lithography." Science, Apr. 7, 2000, vol. 288, pp. 113-116.

Yu, Hongmei et al. "A plate reader-compatible microchannel array for cell biology assays." Lab on a Chip, 2007, vol. 7, pp. 388-391.

Fan, Shih-Kang, et al. "Cross-scale electric manipulations of cells and droplets by frequency-modulated dielectrophoresis and electrowetting." Lab on a Chip, 2008, vol. 8, pp. 1325-1331.

Chen, Ting-Hsuan et al. "Selective Wettability Assisted Nanoliter Sample Generation Via Electrowetting-Based Transportation." Proceedings of the Fifth International Conference on Nanochannels, Microchannels and Ninichanneis, Jun. 18-20, 2007, pp. 1-7.

Swinbanks, D., Government backs proteome proposal, Nature, 1995, vol. 378, No. 6558, p. 653.

Zergioti et al, Femtosecond laser microprinting of biomaterials, Applied Physics Letters, 2005, vol. 86, pp. 163902-1-163902-3.

Abdelgawad, Mohamed et al, Low-cost, rapid-prototyping of digital microfluidics devices, Microfluid Nanofluid (2008), vol. 4, pp. 439-455.

Chuang et al, Direct Handwriting Manipulation . . . Dielectric Sheet, (2006), IEEE MEMS, pp. 538-541, Istanbul, Turkey.

Jebrail, Mais J. et al, Digital Microfluidic Method for Protein Extraction by Precipitation, (2008), American Chem., vol. 81, pp. 330-335.

Lebrasseur, Eric et al, Two-dimensional electrostatic.. plastic film card, (2007) Sensors and Actuators A, vol. 136, pp. 358-366.

Lee, Eun Zoo et al, Removal of bovine serum . . . microfluidic device, (2008), Journal of Chromatography A., vol. 1187, pp. 11-17.

Tan, Hsih Yin et al, A lab-on-a-chip for detection of nerve agent sarin in blood, (2008), Lab Chip, vol. 8, pp. 885-891.

Barbulovic-Nad, and Wheeler, A.R., Cell-Based Assays on Digital Microfluidic Devices, poster at Biomedical Engineering Society (BMES) Meeting, Los Angeles, CA, Sep. 28, 2007.

Chao Yung Fan, et al., "Electrically Programmable Surfaces for Configurable Patterning of Cells." Advanced Materials, 2008, 20, 1418-1423.

* cited by examiner

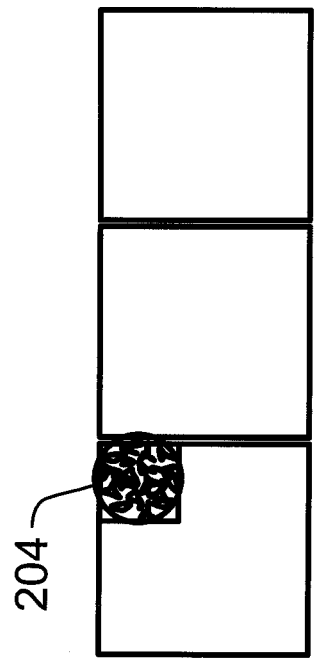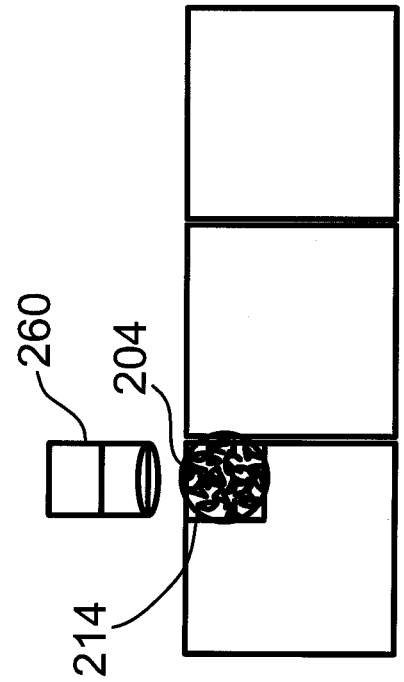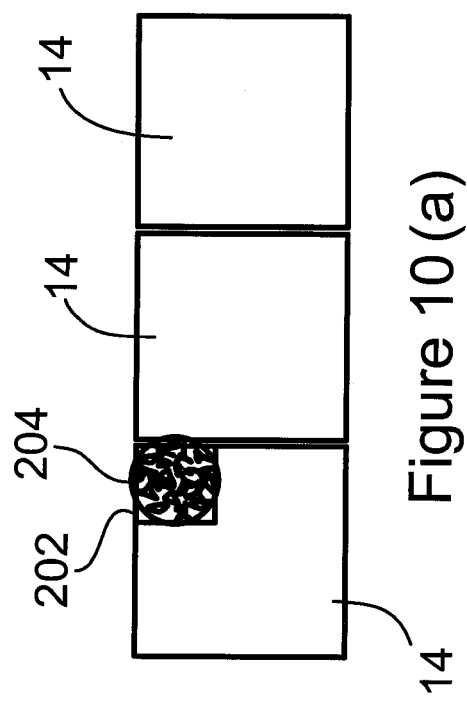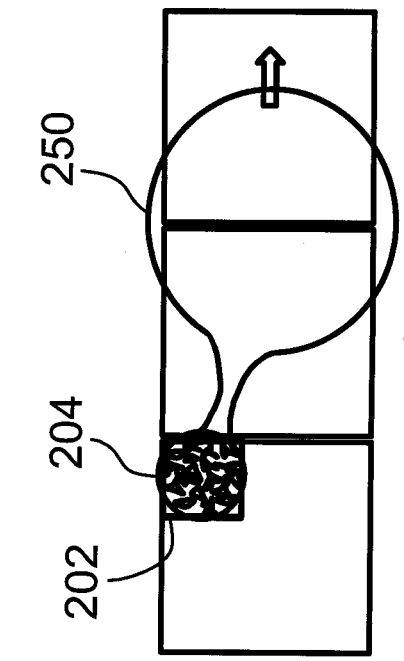

CELL CULTURE AND CELL ASSAYS USING DIGITAL MICROFLUIDICS

CROSS REFERENCE TO RELATED U.S. APPLICATIONS

This patent application is the National Phase of International Application No. PCT/CA2008/002040, filed Nov. 20, 2008, which is a continuation-in-part of U.S. application Ser. No. 12/285,020, filed on Sep. 26, 2008, (now U.S. Pat. No. 8,367,370) and which claims priority benefit from U.S. Provisional Patent Application Ser. No. 61/064,002 filed on Feb. 11, 2008, in English, entitled DROPLET-BASED CELL ASSAYS, both of which are incorporated herein by reference in their entirety.

FIELD OF THE INVENTION

The present invention relates to droplet-based cell assays and/or cell culture using digital microfluidics, and more particularly, the present invention relates to devices and methods used with those devices for performing cell assays and/or cell culture.

BACKGROUND OF THE INVENTION

The cell is the irreducible element of life and is often studied as a living model of complex biological systems. Cells are often studied in vitro, i.e. in culture, in a homogeneous medium either suspended (anchorage independent cells) or attached to a surface (anchorage dependent cells). The majority of mammalian cells are anchorage dependent, i.e. adherent. In culture, they grow in layers usually attached to plasticware (tissue culture polystyrene) in cell culture growth media under controlled conditions (incubators with humidified atmosphere at 37° C. with 5% $CO_2$). Adherent cells often divide until the surface on which they are attached is fully covered—they divide and cumulate to form a confluent monolayer. Upon reaching confluency, cells are subcultured (i.e., passaged, split), by harvesting and splitting the population of cells into smaller populations that are further cultured. Some cultures are semi-adherent, and grow as a mixed population where a proportion of cells does not attach to the tissue culture flask and remains in suspension. To maintain this heterogeneous population both the attached cells and the cells in suspension must be subcultured.

Cell-based assays are conventionally performed in well plates that enable simultaneous analysis of multiple cell types or stimuli. For such multiplexed analyses, cells are cultured and assayed in wells holding microliter-milliliter volumes. Cell response to stimuli in well plates is often evaluated using microplate readers, which can be integrated with fluid handling and other miscellaneous equipment in a robotic analysis platform. A major drawback of such systems is the expense of the instrumentation and the experimental consumables (e.g., plates, pipette tips, reagents, and cells). The latter is a particular disadvantage for cell-based assays as they are generally more complex and require larger amounts of reagents than cell-free assays.[1]

Recently, microfluidics has been touted as a solution to the challenges inherent in conducting multiplexed cell-based assays.[2] The conventional format for microfluidics, which is characterized by devices containing networks of micron-dimension channels, allows integration of multiple processes on a single platform while reducing reagent consumption and analysis time. There are numerous advantages of using microfluidic based systems for cell assays, some of which are self-similarity in dimensions of cells and microchannels (10-100 μm widths and depths), laminar flow dominance and formation of highly resolved chemical gradients, subcellular delivery of stimuli, reduced dilution of analytes, and favorable scaling of electrical and magnetic fields. For the last ten years, researchers have used microchannels to manipulate and sort cells, to analyze cell lysates, to assay intact-cell biochemistry, and to evaluate cell mechanical and electrical responses. In most of these studies, cells were exposed to one stimulus or to a limited number of stimuli.

There have been just a few attempts to conduct multiplexed assays as it is difficult to control many reagents simultaneously in a complex network of connected channels, even when using microvalve architectures developed for microfluidic devices.[3] In addition, there have been only a few microfluidic devices integrated to multiplexed detection instruments such as microplate readers;[4] we believe this will be a necessary step for the technology to become competitive with robotic screening systems. Finally, we note that advancements have been made towards long-term cell culture and cell assays in microfluidic systems; however, there are no reports on passaging cells in microchannels or in other microsystems.

A potential solution to the limitations of the channel-microfluidic format is the use of "digital" or droplet-based microfluidics. In digital microfluidics (DMF), discrete droplets containing reagents are manipulated by sequentially applying potentials to adjacent electrodes in an array.[5-14] Droplets can be manipulated independently or in parallel on a reconfigurable path defined by the electrode actuation sequence, which allows for precise spatial and temporal control over reagents. As with all microscale techniques, cross-contamination is a concern for DMF, but this phenomenon can be avoided by dedicating separate paths for each reagent. DMF has been used to actuate a wide range of volumes (nL to μL) and, unlike channel devices, there is no sample wasted in creating small plugs for analysis. In addition, each droplet is isolated from its surroundings rather than being embedded in a stream of fluid—a simple method of forming a microreactor in which there is no possibility that products will diffuse away. The preservation of products in a droplet is of great importance in cell assays targeting molecules secreted from cells into extracellular space. In addition, droplets provide mostly static fluid conditions without unwanted shear stress that is inevitable in continuous flow microfluidics. A further advantage of DMF is its capacity to generate nanoliter samples by translating droplets through selective wettability areas on an electrowetting-based platform.[15]

There is currently much enthusiasm for using DMF to implement multiplexed assays; however, it has only been applied to a few non-cell assays. To the inventors' knowledge, there are no reports of the use of DMF to analyze cells. There are a few studies demonstrating only dispensing and manipulation of droplets containing cells, cell sorting, and cell concentration on a DMF platform. WO 2007/120241 A2 entitled "Droplet-Based Biochemistry"[16] discloses dispensing and dividing droplets containing cells, generating droplets with single cells, detecting a type of cell, and sorting cells. US20070148763 A1 entitled "Quantitative cell dispensing apparatus using liquid drop manipulation"[17] describes cell droplet handling, to achieve a predetermined number of cells. In a journal paper by Fan et al,[18] dielectrophoresis was used to concentrate neuroblastoma cells within droplets on a DMF platform.

It would be very advantageous to provide droplet-based cell culture and/or assays using digital microfluidics in order to enable automated cell micro-culture and high-throughput screening ability for cell analysis. DMF has a high potential to address many problems associated with standard culture and assaying in well-plates or in continuous-flow microfluidic devices.

SUMMARY OF INVENTION

The present invention provides embodiments of devices and methods for droplet-based cell culture and cell assays using digital microfluidic devices designed to manipulate, operate, and analyze cell-containing droplets. Suspension of cells and cell-assay and/or cell-culture reagents are deposited in the device by either dispensing them from device reservoirs, by dispensing them from external reservoirs in fluid communication with a device, or by dispensing them into the device using external dispensing means (e.g., pipette, robotic dispenser, etc.).

After being introduced in a device in suspension, cells are seeded on cell culture sites, where they are long-term cultured in droplets, subcultured using standard subculture protocols, and assayed. A cell culture site is a patterned surface of a DMF device that enables cell attachment to a device surface. Media exchange and regent delivery on cell culture sites (CCSs) is performed using standard DMF operations: translating, merging, mixing and splitting droplets. In addition, a new technique, passive dispensing, is developed for more efficient delivery of reagents/media from a big source droplet translating over CCSs. By means of DMF and passive dispensing, a first multigenerational cell culture in a microscale is realized.

Culture and assay reagents comprise chemical, biochemical and biological reagents. Droplets contain additives including pluronics and various hydrophilic polymers to facilitate cell-containing droplet actuation by preventing non-specific adsorption of cells and proteins to a device surface.

In a multiplexed assay, multiple cell-containing droplets (which may include one kind or multiple kinds of cells) are manipulated and assayed simultaneously or in a certain sequence with one or multiple reagents. Embodiments of the present invention provide a digital microfluidic device for conducting cell assays and cell culture, comprising:
a first substrate having a first substrate surface;
a first array of discrete electrodes located on the first substrate surface;
at least one coating formed on the first substrate surface covering each discrete electrode such that the discrete electrodes are electrically insulated from one another, an outer surface of the at least one coating formed on the first substrate surface forming a working surface, the working surface including one or more pre-selected positions having cell culture sites located thereon;
an electrode controller connected to the discrete electrodes capable of selectively activating or de-activating each of said discrete electrodes for translating liquid droplets across said working surface, said electrode controller being connected to a reference electrode means; and
wherein said one or more pre-selected positions with cell culture sites thereon are located such that each of said one or more cell culture sites is accessible to liquid droplets being translated by said first array of discrete electrodes.

Embodiments of the invention also provide a digital microfluidic device for conducting cell assays and cell culture, comprising:
a first substrate having a first substrate surface;
a first array of discrete electrodes formed on the first substrate surface;
at least one coating formed on the first substrate surface covering each discrete electrode such that the discrete electrodes are electrically insulated from one another, an outer surface of the at least one coating formed on the first substrate surface forming a first working surface;
a second substrate having a second substrate surface which is hydrophobic forming a second working surface, wherein the second substrate is in a spaced relationship to the first substrate thus defining a space between the first and second substrates capable of containing liquid droplets between the first and second working surfaces;
one or both of the first and second working surfaces including one or more pre-selected positions having cell culture sites located thereon; and
an electrode controller connected to the discrete electrodes capable of selectively activating or de-activating each of said discrete electrodes for translating liquid droplets across the first and second working surfaces, said electrode controller being connected to a reference electrode means, and wherein said one or more pre-selected positions with cell culture sites thereon are located such that each of said one or more cell culture sites is accessible to liquid droplets being translated by said first array of discrete electrodes between said first and second working surfaces.

The present invention also provides a digital microfluidic based method of performing any one or both of cell assays and cell culture, comprising the steps of:
a) providing a digital microfluidic device having an array of discrete electrodes formed on a first substrate surface, a coating having a working surface formed on the first substrate surface and array of discrete electrodes, an electrode controller for activating or de-activating said discrete electrodes for translating liquid droplets over said working surface, said electrode controller being connected to a reference electrode means;
a(i) optionally including a second substrate with a hydrophobic surface, wherein when present the second substrate is in a spaced relationship to the first substrate thus defining a space between the first substrate and second substrate capable of containing liquid droplets between the hydrophobic surface of the second substrate and the working surface on the first substrate;
b) when said second substrate is not present, modifying one or more pre-selected positions on said working surface, to produce one or more cell culture sites wherein said one or more cell culture sites are located such that each cell culture site is accessible to liquid droplets being translated by said electrode array;
b(i) and when said second substrate is present, modifying one or more pre-selected positions on said working surface alone, or modifying one or more pre-selected positions on said hydrophobic surface alone, or modifying one or more pre-selected positions on both said working surface and said hydrophobic surface;
c) dispensing one or more first liquid droplets containing a suspension of at least one kind of cells in a cell medium onto one or more first positions on the working surface, and optionally dispensing one or more second liquid droplets containing cell assay/cell culture reagents onto one or more second positions on the working surface;
d) translating at least the one or more first liquid droplets to said one or more corresponding cell culture sites, and optionally translating at least the one or more second liquid droplets to said one or more corresponding cell culture sites;

e) incubating the cells at each said one or more cell culture sites in an incubation medium contained either in said first liquid droplets or in said second liquid droplets or in a mixture thereof; and f) analyzing the one or more cell culture sites to characterize one or both of the cells and cell medium in each culture site.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIGS. 10(a) to (d) show diagrammatic representations of assaying adherent cells in a DMF device where, (a) shows a monolayer of adherent cells cultured on a CCS in cell culture media, (b) washing cells and delivering assay reagents to cells via passive exchange, (c) incubating cells with assay reagents, and (d) detecting and analyzing cell response to assay stimuli.

DETAILED DESCRIPTION OF THE INVENTION

Without limitation, the majority of the systems described herein are directed to methods and devices for droplet-based cell assays using digital microfluidics. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to droplet-based cell assays and culture using digital microfluidics (DMF).

As used herein, the term "about" and the symbol "~", when used in conjunction with ranges of dimensions, temperatures or other physical and/or chemical properties and/or characteristics is meant to cover slight variations that may exist in the upper and lower limits of the ranges of dimensions as to not exclude embodiments where on average most of the dimensions are satisfied but where statistically dimensions may exist outside this region. For example, in embodiments of the present invention dimensions of a digital microfluidic device are given but it will be understood that these are not meant to be limiting. Herein, term "adherent cells" refer to both adherent and semi-adherent cell types.

Figure 1:
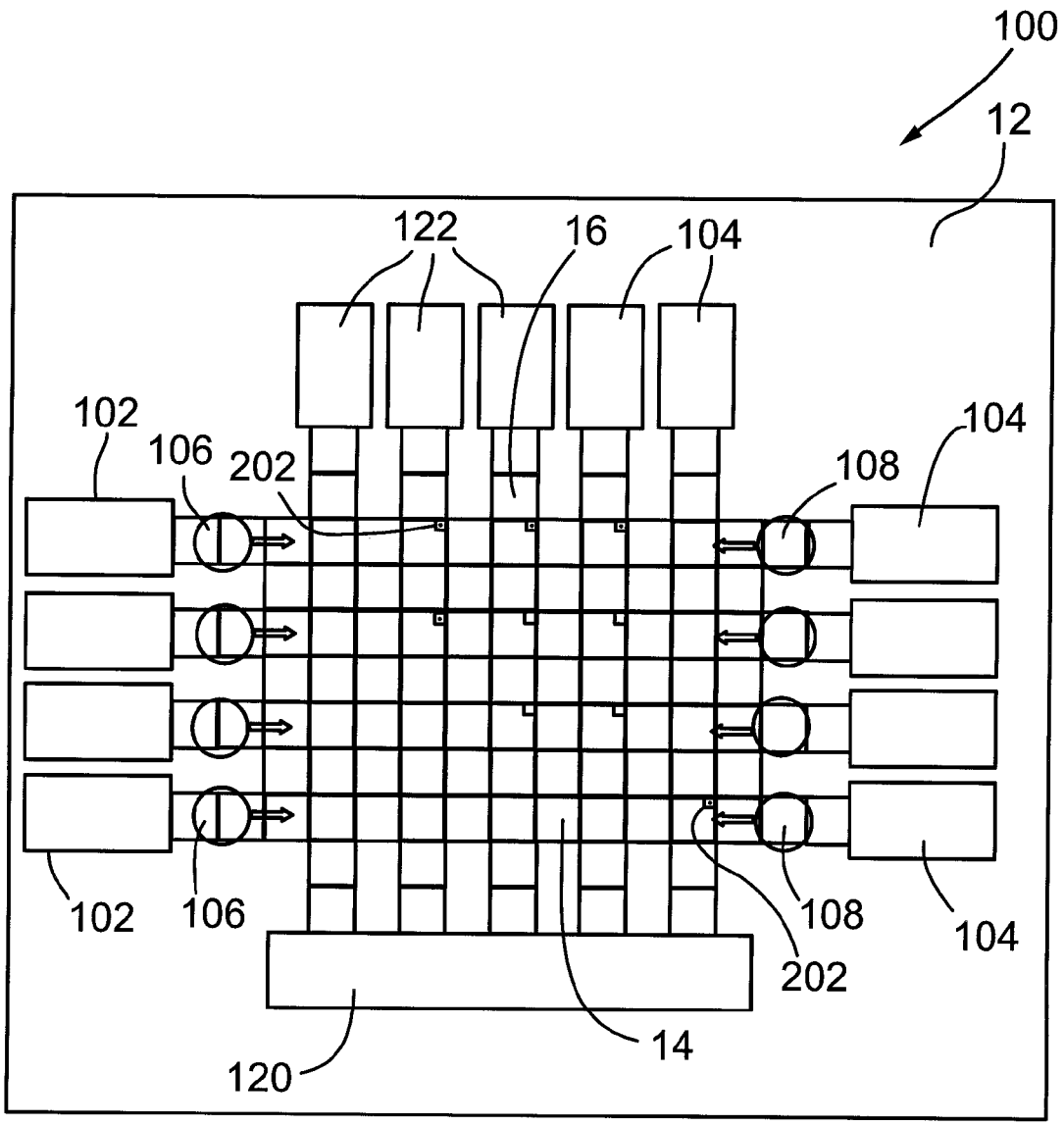
FIG. 1 shows a top view of an embodiment of a DMF device for multiplexed adherent cell assays which comprises reservoirs for four different cell suspensions, six different assay reagents, three different washing solutions, and a waste reservoir.

Referring to FIG. 1, a top view of a DMF device 100 configured for adherent cell assays includes a substrate 12 on which an electrode array comprised of discrete electrodes 14 is mounted. In flow communication with the array of electrodes 14 is a waste container 120 into which all liquid waste can be translated once the assay is complete or as required. Reservoirs 122 may contain cell washing solutions and solutions for cleaning the surface of the device between assay steps. Multiple reservoirs 102 may contain different cell suspensions and reservoirs 104 may contain cell assay reagents. Droplets of cell suspension 106 and droplets of cell assay/culture reagents 108 can be deposited in the device either by dispensing them from device reservoirs 102 (cells) and 104 (reagents), by dispensing them from external reservoirs in fluid communication with the device, or by dispensing them using external means (e.g., pipette, robotic dispenser, etc.), not shown herein. DMF device 100 includes a plurality of cell culture sites 202 where cells in droplets 106 are seeded and maintained for further culture or analysis. Cell assays and cell culture are performed by exposing cells on cell culture sites 202 to assay/culture reagents in droplets 108.

Figure 2:
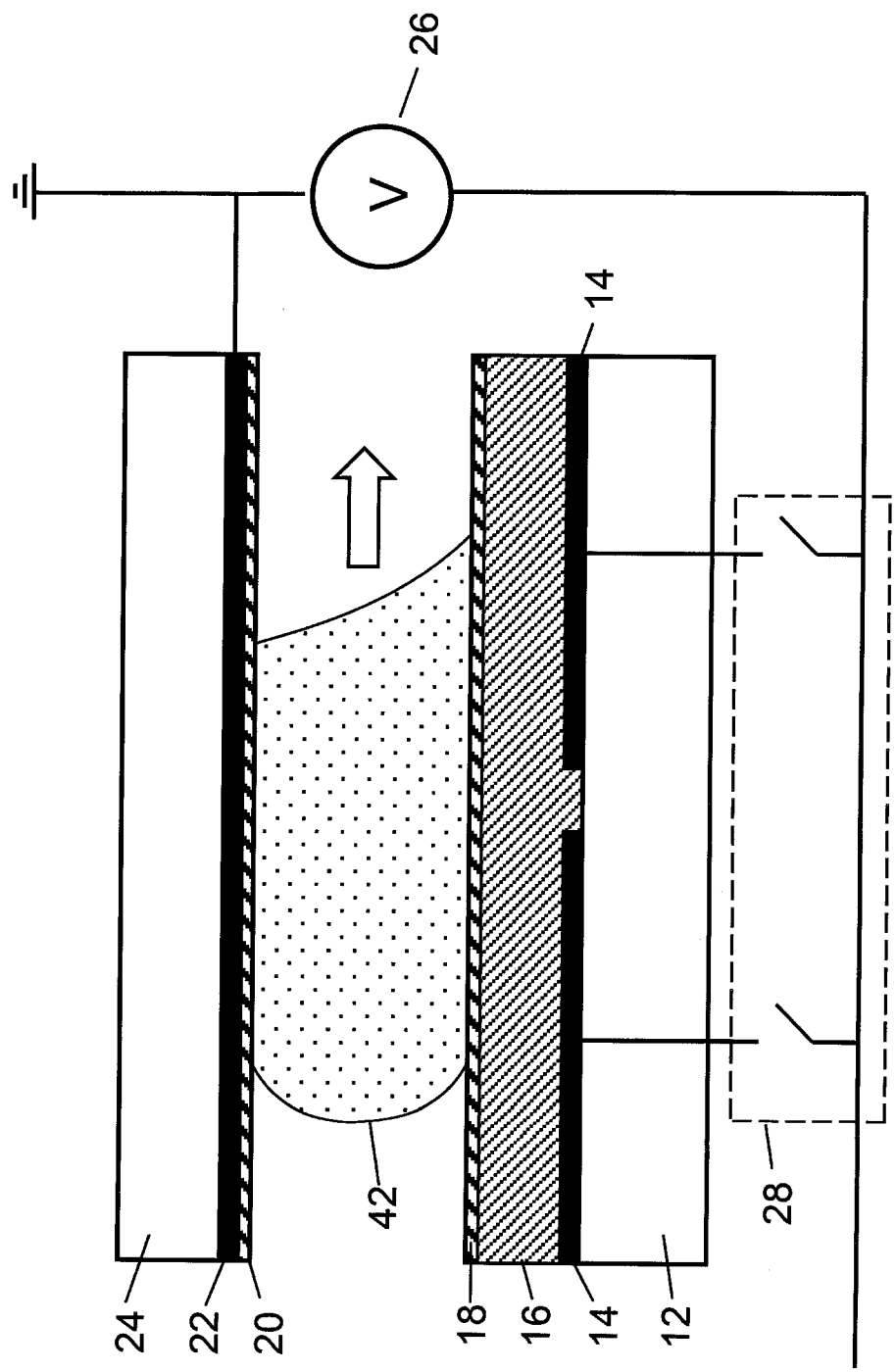
FIG. 2(a) shows a cross-sectional view of the device of FIG. 1.
FIG. 2(b) shows a cross sectional view of an alternative embodiment of the device of FIG. 1 which uses a one-plate design.
Figure 2:
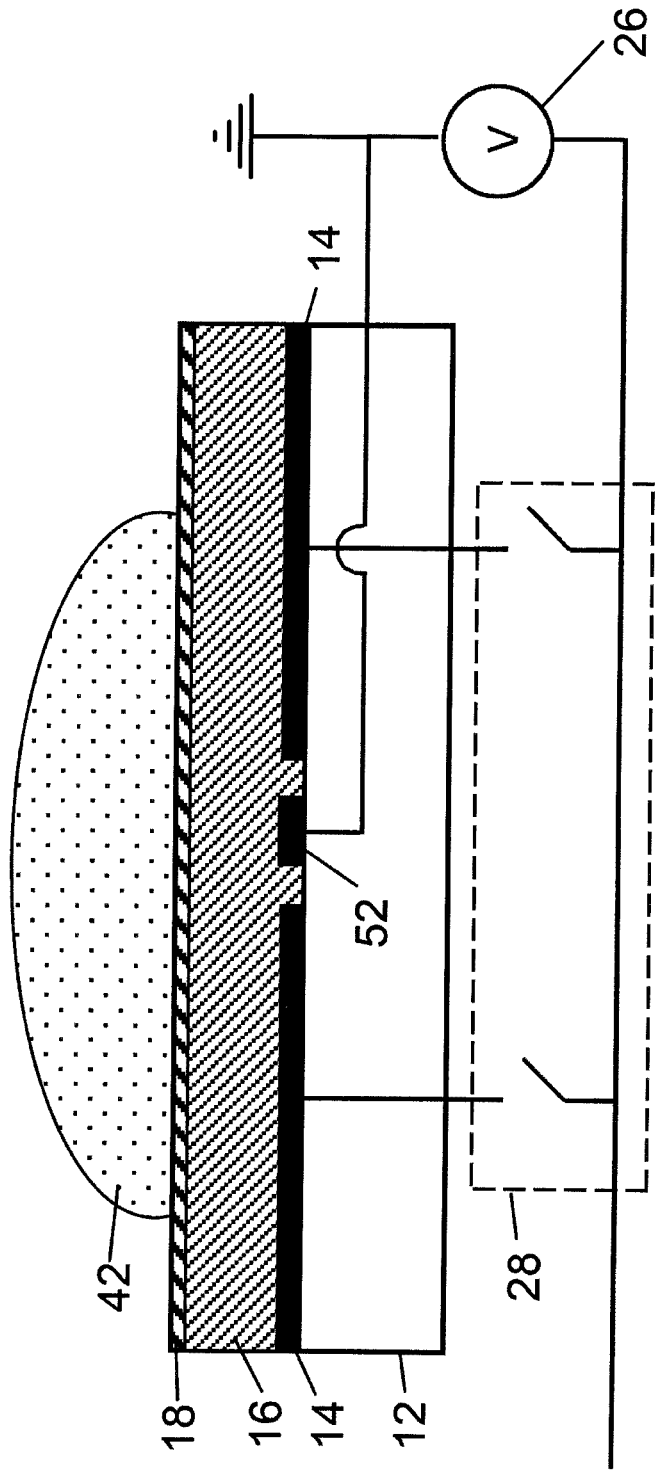

FIG. 2(a) is a cross-sectional view of a portion of the microfluidic device 100 of FIG. 1 showing two adjacent electrodes 14 of the electrode array. Electrodes 14 (for example 10 nm Cr+, 100 nm Au) rest on a substrate layer 12 and are separated from each other by a dielectric material 16 (for example 2 µm Parylene-C). The device can have more than one dielectric layer 16. Located on top of dielectric material 16 is a hydrophobic layer 18 (for example Teflon AF, 50 nm). The top surface of the hydrophobic top layer 18 forms the working surface of the device over which droplets are translated. Spaced above electrodes 14/dielectric layer 16 is a continuous reference electrode 22 deposited on a substrate layer 24, and a hydrophobic layer 20 (for example Teflon AF, 50 nm) is coated on reference electrode 22. Alternatively, another dielectric layer can be deposited between layers 20, 22. Liquid droplets 42 translate in-between two hydrophobic layers 18 and 20. Electrodes 14, voltage source 26, and the continuous reference electrode 22 together form an electric field, digitally manipulated by electrode electrical controller 28. For droplet manipulation, reference electrodes 22 are biased to a potential different from the actuating potential. Commonly used reference potential is ground. Controller 28 may in turn be connected or interfaced to a control means with the control means being programmed to translate liquid droplets of cell suspensions and droplets of reagents in a selected order defined by a selected cell assay protocol or cell culture protocol for which the control means is programmed. The control means may be a computer or computer processor/microprocessor or dedicated control unit preprogrammed.

In a preferred embodiment of the present invention, the upper hydrophobic layer 20, reference electrode 22, and substrate layer 24 are substantially transparent to allow optical analysis of the assays. Furthermore, layers 20, 22, and 24 are not necessary to translate droplets.

While the present invention discusses the two-plate design of FIG. 2(a), a one-plate design is also possible, as shown in FIG. 2(b). In FIG. 2(b), layers 20, 22, and 24 are removed. Rather than have a dedicated reference electrode layer 22, the reference electrode is patterned adjacent to electrodes 14, forming a continuous grid 52 separated from electrodes 14 by dielectric material 16. The continuous grid 52 extends in both directions defining the plane in which electrodes 14 are located.

Reference electrodes can also be coplanar with the top surface of the dielectric layer. In a device with multiple dielectric layers, reference electrodes can be coplanar with the top surface of any dielectric layer, while being insulated from actuating electrodes 14. The design of the reference electrodes is not limited to a grid, e.g. they can be in a form of a wire or an array similarly to electrodes 14.

A challenge for using DMF for manipulation of cells is droplet evaporation, which raises the concentration of salts and other buffer constituents, making the solution hypertonic. Evaporation can be controlled by positioning devices in a humidified atmosphere when not actively manipulating droplets by DMF. For the duration of the short-term assay experiments (up to a few hours), such measures prevented significant evaporation, and have no negative effects on cell viability. For culturing cells and long-term assays, DMF devices can be placed in cell culture incubators (37° C., 5% $CO_2$, 100% humidity). The DMF devices may be contained in a sterile, humidified chamber with controlled conditions for the full duration of the assay or cell culture process (including actuation, incubation, and analysis) which facilitates long-term cell culture and examination.

It should be noted that the assays and culture performed in accordance with the present invention can involve all of dispensing, translating, merging and mixing of droplets, including droplet splitting. Droplet splitting is implemented to reduce a droplet size, number of cells in a droplet, etc.

The present invention may be used to assay droplets containing multiple kinds of cells (e.g., different cell types, or different phenotypes of the same cell type). Droplets with multiple kinds of cells can be generated by either dispensing them from reservoirs containing the same mixed population of cells, or by combining droplets containing one or several kinds of cells. Combining droplets, merging and mixing, results in larger droplets which can be split in droplets of desired size.

Concentration of cells in a droplet can be controlled by the concentration of cells in a source (a device reservoir or an external reservoir) or by combining droplets of suspended cells with droplets of cell suspension medium. In this way, concentration of cells is reduced by the ratio of the combined volumes. The combined droplet can be split in smaller droplets which can be further merged with cell suspension medium for additional cell concentration reduction. By repeating the procedure above, droplets with single cells can be generated and used in single-cell assays.

Some cell assays target molecules that cells secrete into their microenvironment, such as growth factors, signaling molecules, and metabolic products. Since DMF droplets of cell suspension are precise, confined volumes where all cell products are preserved, they are ideal microenvironment for extracellular biochemical assays. In these assays, signal is detected from a medium in which cells are cultured/assayed rather than from cells. A medium can be analyzed by immunoassays or other means. Droplets of cell medium can alternatively be removed from a DMF device and analyzed externally.

Cell Culture Sites

As shown in FIGS. 3(a), 3(b), 3(c), and 3(d), the surface of a DMF device 200 (specifically the hydrophobic surface 18 that covers the dielectric material 16 on the lower electrode 14 (see FIG. 2(a)) is modified in specific areas, cell culture sites (CCS) 202, to facilitate cell adhesion. The surface modification procedure may include standard techniques, such as depositing (microprinting, micorstamping) a bio-substrate 206 (typically extracellular matrix proteins), rendering its surface hydrophilic and charged via microfabrication, or any other surface modification procedure that can also be cell specific. In addition to using standard techniques, a bio-substrate can be formed by dispensing a droplet of dissolved bio-substrate in a DMF device and translating it to the cell culture site 202, where after incubation and drying, it forms a bio-substrate layer for cell attachment. In this case, a device can have an extra reservoir containing the bio-substrate solution.

Figure 3A:
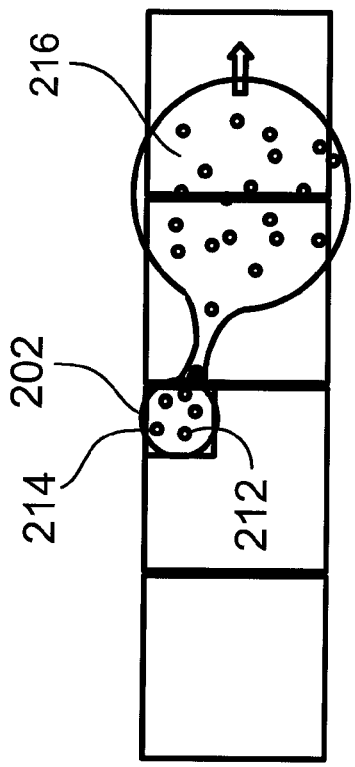
FIGS. 3(a) to (g) are diagrammatic representations of seeding cells in a DMF device where (a) shows actively dispensing a droplet of cell suspension translating to a cell culture site (CCS), (b) shows passively dispensing a droplet of cell suspension onto the CCS from a source droplet, (c) shows cells in suspension seeded on the CCS, (d) shows monolayer of adhered cells formed on the extracellular matrix (ECM) substrate on the CCS; (e) shows an embodiment in which the CCS is located on the second subsrate, (f) shows an embodiment in which cell culture sites are located on both the top and bottom plates at a common location, and (g) shows an embodiment in which cell culture sites are located on both the top and bottom plates at different locations.
Figure 3B:
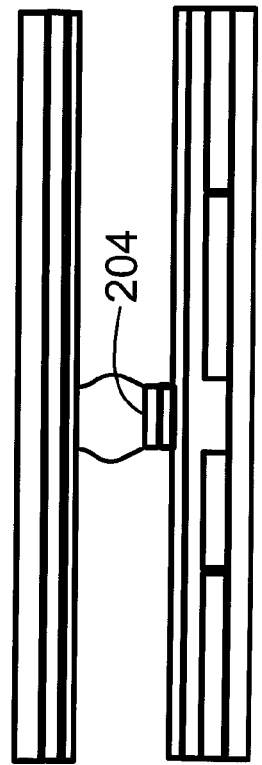
Figure 3C:
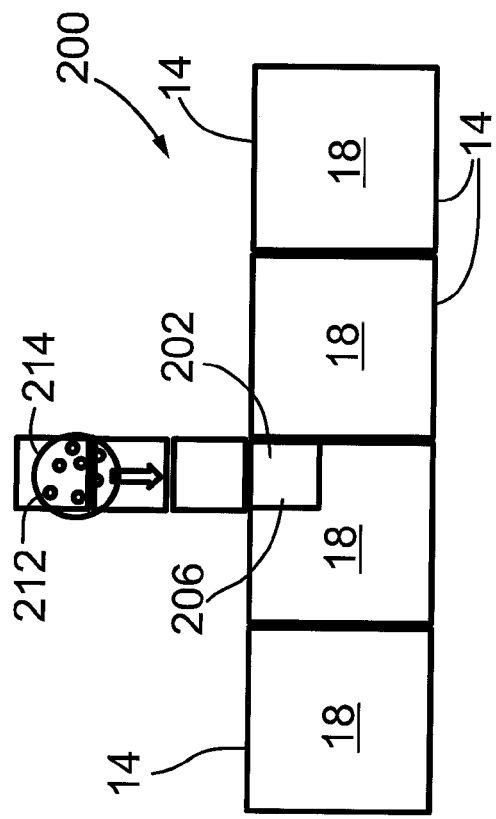

After the cell culture site 202 is formed, cells are seeded by generating a droplet 214 of growth media with suspended cells 212 on the cell culture site 202 (FIG. 3(c)). Anchorage dependent cells are allowed to adhere to the surface forming a cell monolayer 204 (FIG. 3(d)), while anchorage independent cells typically remain in suspension at the cell culture site 202. There are two DMF ways of generating a droplet 214 on the cell culture sites 202: (1) by actively dispensing a droplet from a device reservoir or via external means (e.g. pipetting) and translating the droplet to the cell culture sites 202 (FIG. 3(a)), and (2) by actuating a droplet 216 (source droplet) larger than the cell culture sites 202 over the cell culture site 202 and thereby passively dispensing the desired droplet on the hydrophilic cell culture site 202 (FIG. 3(b)). Passive dispensing will be described in more details in the following section. It should be noted that cells can be seeded by dispensing a cell-containing droplet via external dispensing means (e.g. pipettes, robotic dispensers, microprinters, microstamps) directly on CCSs.

Passive Dispensing, Passive Washing, Passive Media/Reagent Exchange

Figure 4:
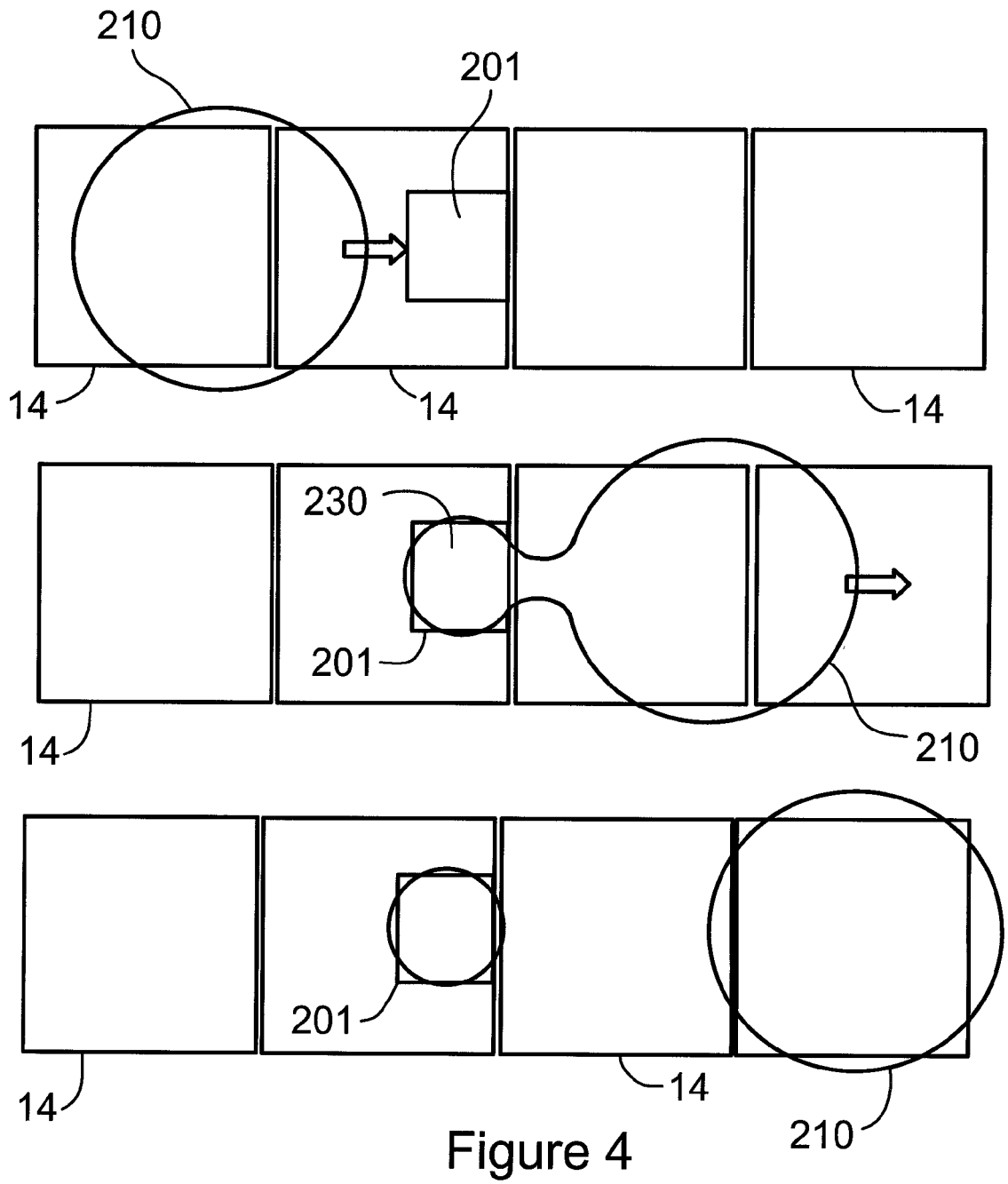
FIG. 4 is a diagrammatic representation showing passive dispensing of a droplet where a source droplet provides a smaller liquid droplet located on the CCS.

Referring to FIG. 4, when a source droplet 210 is actuated in a DMF device over a patterned hydrophilic area 201 smaller than the base area of the source droplet 210, it leaves behind a smaller droplet 230 on the hydrophilic area 201 as the rest of source droplet 210 is translated away from the hydrophilic area 201. This method of generating droplets is termed passive dispensing. Hydrophilic areas 201 are produced by methods that include but are not limited to microfabrication techniques (e.g. exposing hydrophilic layers of a device, such as glass or electrodes), surface chemistry modification methods including hydrophobic surface plasma treatment, or deposition of a thin, patterned, hydrophilic layer onto a device surface.

Hydrophilic areas can be formed on either the top plate, the bottom plate, or both the top and bottom plates of a two-plate device, as shown in FIGS. 3(c)-3(g).

In the applications disclosed herein of cell culture and assaying, hydrophilic areas 201 are used as the cell culturing sites (indicated by reference numeral 202 in FIG. 3(a)) which are preferably patterned by depositing bio-substrates, made from cell specific constituents, such as, but not limited to, extracellular matrix (ECM) proteins. ECMs are more favorable substrate for cell attachment than bare glass, exposed electrodes, or a dielectric layer, as they are constituents of cells' natural environment. Examples of extracellular matrix proteins include, but are not limited to fibronectin, laminin, collagen, elastin. The cell specific constituents may also comprise synthetic molecules comprised of one of poly-L-lysine, poly-D-lysine and any combination thereof for example. Growth of some cells completely depends on the physical contact with other cells so CCSs have to be first seeded with a layer of feeder cells (usually adherent growth-arrested cells) which is then used as a substrate for seeding cells of interest. For example, feeder layer cells are used for safe and robust culturing of human and mouse embryonic stem cells.

Typically, there are no electrodes underneath hydrophilic areas, as these areas (inherently hydrophilic) do not need to be electrically addressed to attract droplets; however, they have to be at least in the vicinity of electrodes to be accessible to droplets translated by electrodes. It will be appreciated that the hydrophilic arrays can also be formed on the top surface of the layer coating electrodes right above electrodes themselves. In most cell-based applications, it is desirable to have a transparent attachment substrate to enable facile cell visualization.

Figure 5:
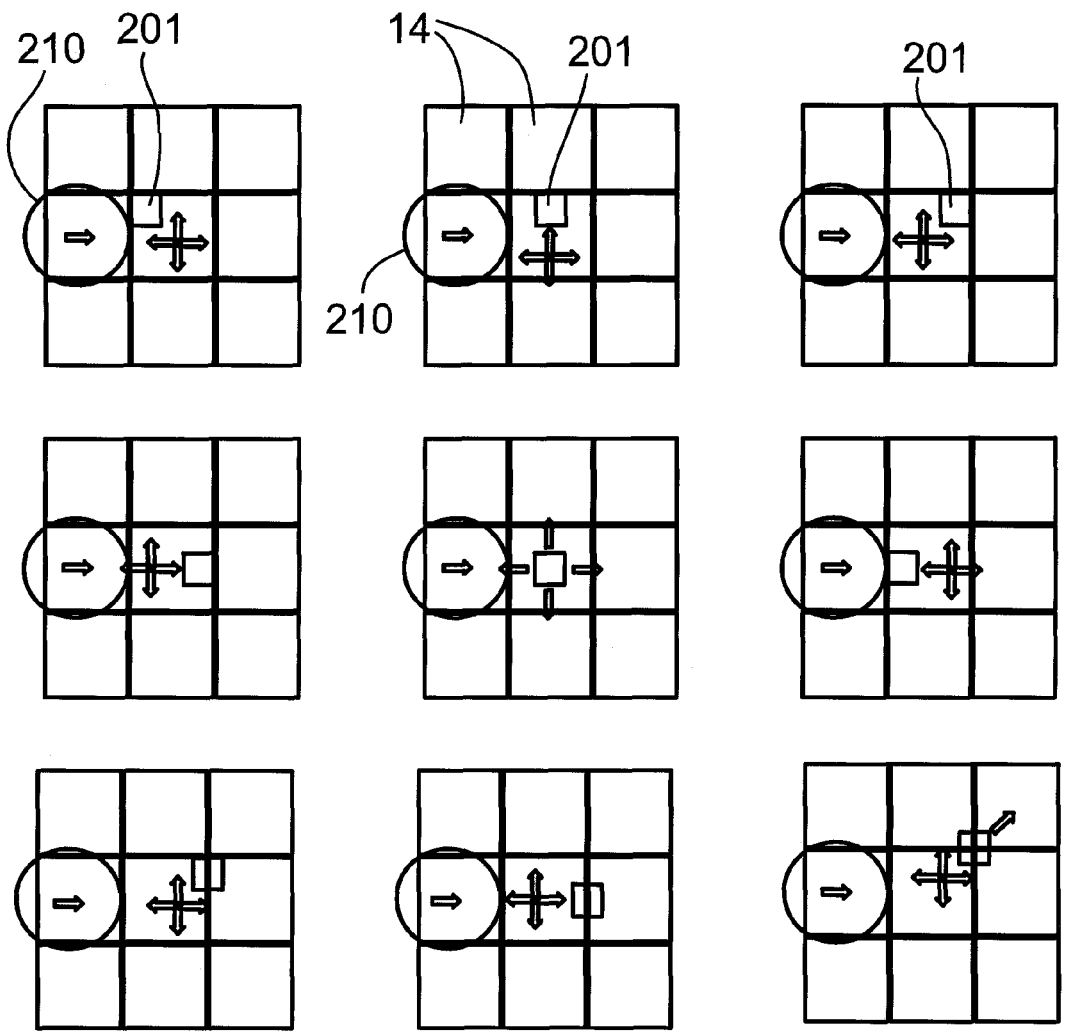
FIG. 5 shows several examples of the hydrophilic area positions relative to actuating electrodes and to the source droplet path.

Referring to FIG. 5, the size and position of a hydrophilic area can vary relative to the size and position of electrodes 14 for source droplets actuation. Two relative sizes of hydrophilic areas, ¼ and ⅑ of the electrode size, and several positions relative to electrodes 14 and to a source droplet path are demonstrated to be efficient in passive dispensing. It should be noted that size and position of hydrophilic areas 201 is not limited by the examples in FIG. 5, and that the shape of hydrophilic areas 201 and actuating electrodes 14 is not limited to the square shape.

Figure 6:
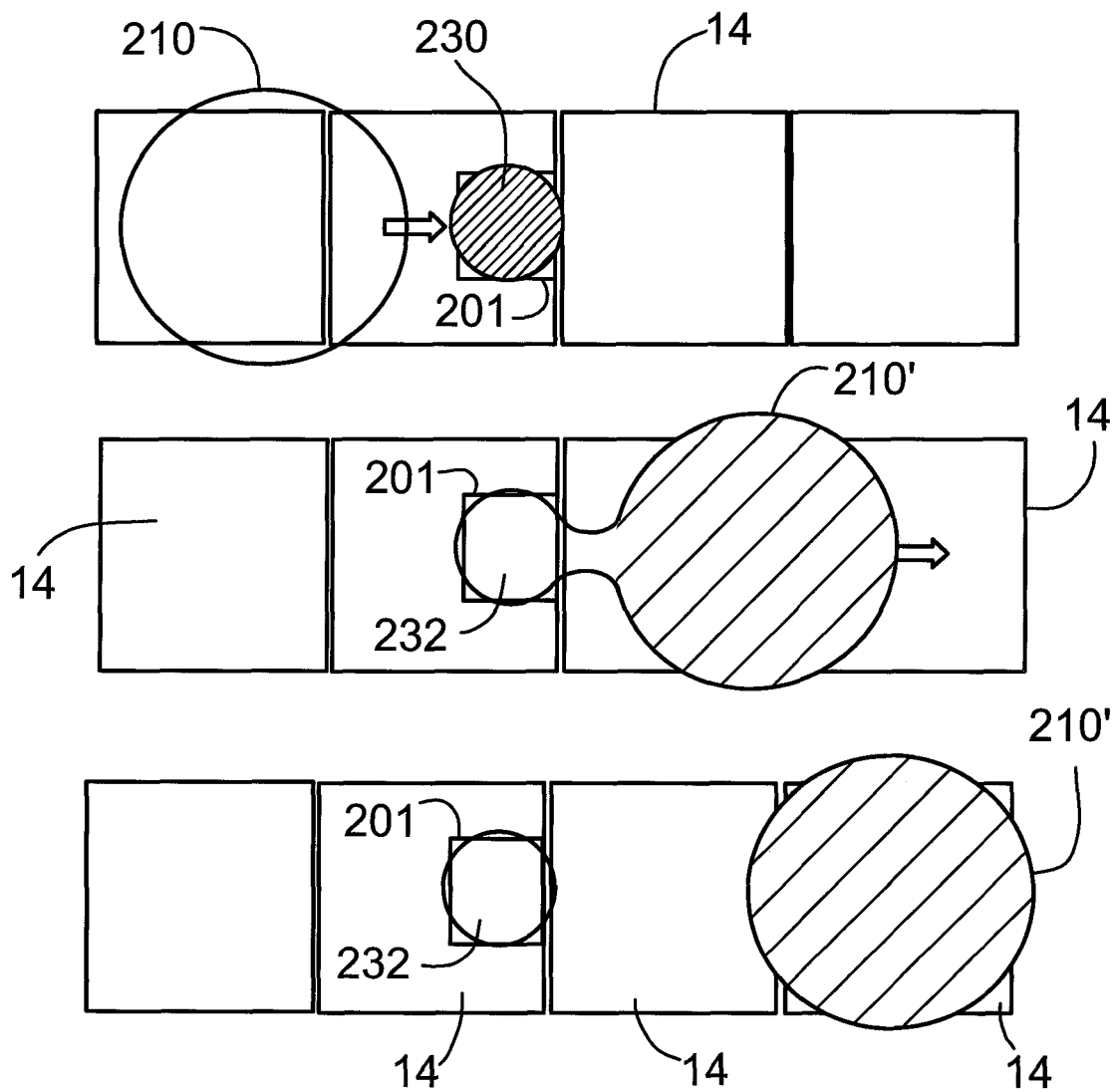
FIG. 6 shows a diagrammatic representation showing a passive washing/exchange process whereby a droplet on a CCS is replaced by a new droplet.
Figure 7:
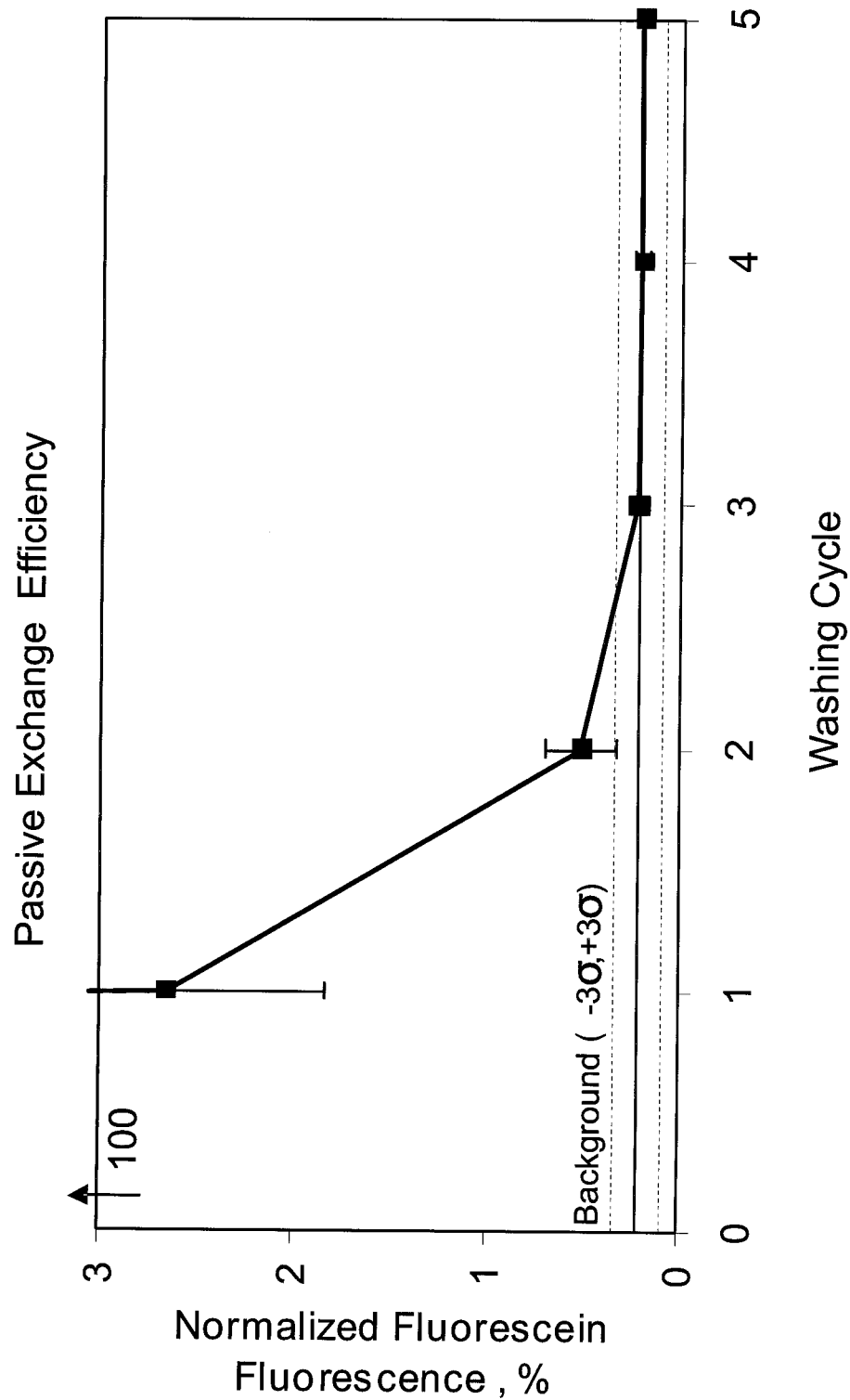
FIG. 7 shows a graph of fluorescein fluorescence signal intensity versus washing cycle to show passive washing/exchange efficiency.

Referring to FIG. 6, when a hydrophilic area 201 is already occupied by a droplet 230, a source droplet 210 will replace it with a new droplet 232 of the source solution while removing the droplet 230 in a droplet 210'. This process is termed passive washing or passive exchange of liquid solutions on hydrophilic areas 201 (e.g., on cell culture sites) in a DMF device. We report passive exchange efficiency of ≥95% with a single source droplet, or ≥99% with two or more consecutive source droplets. FIG. 7 shows efficiency of 0.5 nM fluorescein passive exchange with phosphate buffered saline. These results were obtained with hydrophilic areas 201 formed of fibronectin occupying ~⅑ of the electrode 14 size, and having two different positions relative to actuating electrodes 14.

Culturing and Passaging Adherent Cells

Figure 3D:
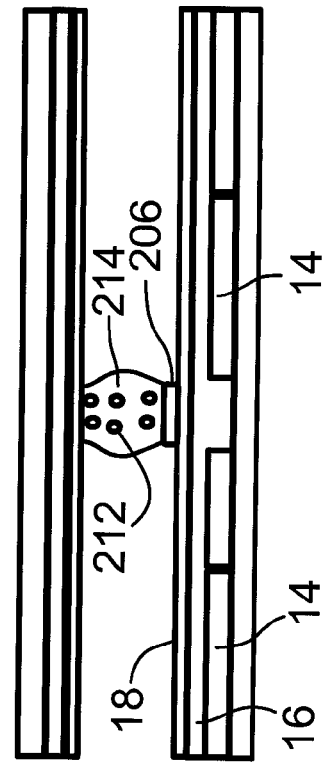
Figure 3E:
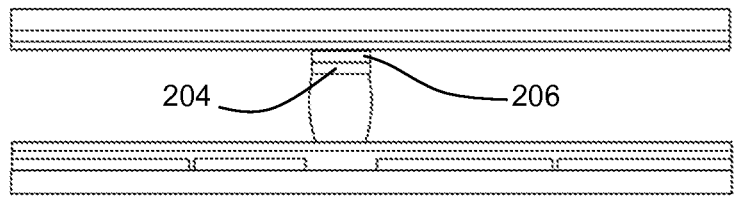
Figure 3F:
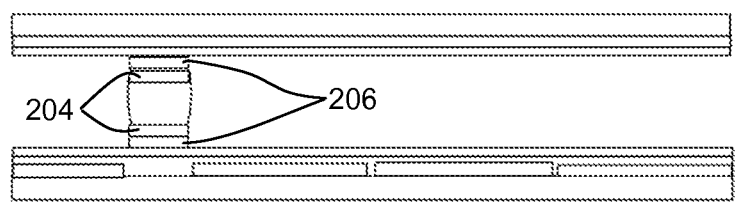
Figure 3G:
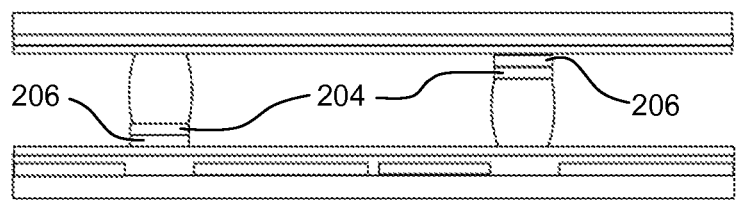
Figure 8:
FIG. 8 shows a digital image of ~130 mouse fibroblast cells (NIH-3T3) cultured in a DMF device for 72 h; medium was replenished using passive exchange technique every 24 h; after 72 h cells were stained with calcein AM for viability.

For adherent cell culture, a DMF device with seeded cells is placed in a cell culture incubator and a droplet of culture media on top of the cell layer 204 (FIG. 3(d)) is regularly replenished with fresh media via DMF passive exchange (usually every 24 h). This method enables long-term culturing of cells on cell culture sites 202 in DMF devices. Thereby, growth characteristics and morphology of the cells are comparable to cells grown in standard tissue culture flasks (FIG. 8); no detachment of cells is observed during media droplet actuation over the cell culture sites 202.

Figure 9A:
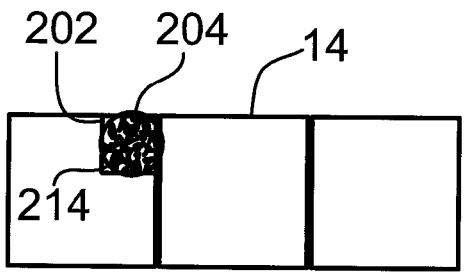
FIGS. 9(a) to (f) are diagrammatic representations of subculturing adherent cells in a DMF device in which (a) shows monolayer of adherent cells cultured on a CCS, (b) washing cells via passive exchange, (c) delivering a dissociation agent to cells via passive exchange, (d) detachment of cells after incubation with the dissociation agent, (e) blocking of the dissociation agent and resuspending cells via passive exchange, and (f) seeding of cells resuspended in fresh media on a new CCS.
Figure 9D:
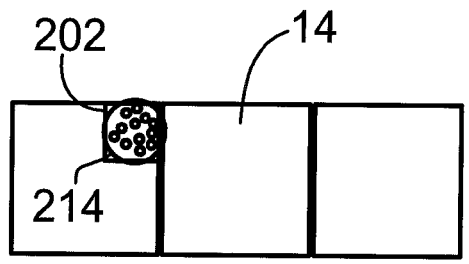
Figure 9B:
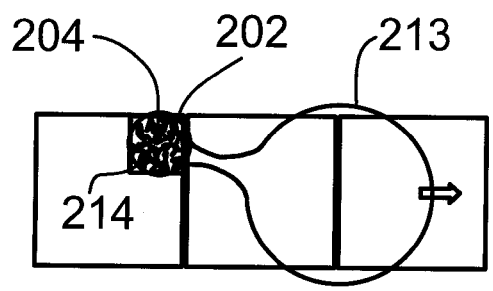
Figure 9E:
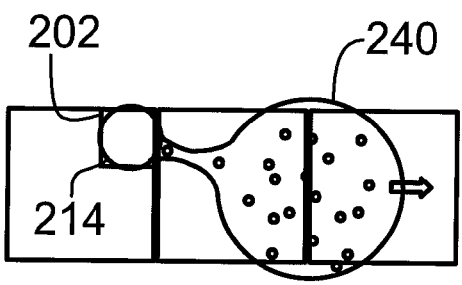
Figure 9C:
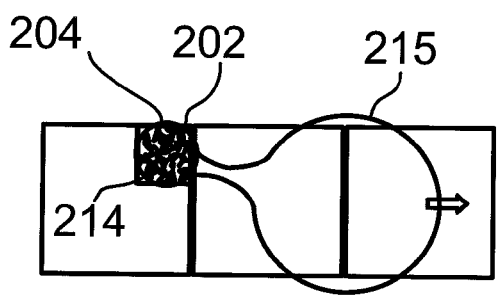
Figure 9F:
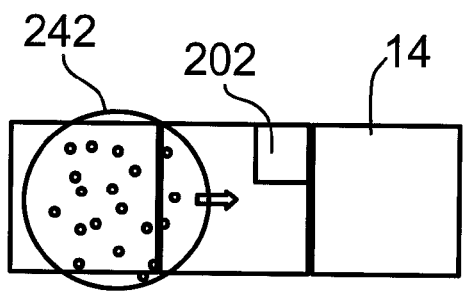

In one embodiment, the invention may provide subculturing (i.e., splitting or passaging) of cells grown on CCSs (FIG. 9(a)) using standard subculturing protocols adapted to a DMF system: (1) washing cells as shown in FIG. 9(b) in which a droplet 213 of a cell washing solution is translated over the cell culture site 202, (2) harvesting cells by translating a droplet 215 containing a dissociation agent (e.g., trypsin, collagenase) over the cell culture site 202 as shown in FIG. 9(c), and incubating cells with the dissociation agent to detach the adhered cells as shown in FIG. 9(d), (3) blocking the dissociation agent with a droplet 240 containing a blocking agent (typically serum in cell culture media) which is translated over cell culture site 202 while it removes the detached cells away from the cell culture sites 202 as shown in FIG. 9(e), (4) splitting the resulting droplet 240 of the cell suspension as necessary and merging the split droplets with fresh media droplet and (5) seeding cells resuspended in media droplet 242 on a new cell culture site 202 as shown in FIG. 9(f).

In the step (3), the cell suspension is diluted in a big source droplet 240 of a blocking agent (typically serum in a cell culture media) by the volume ratio of the two droplets, cell culture site 202 droplet 214 and the source droplet 240. In the step (4), the resulting cell suspension can be split in smaller droplets which can be then merged with droplets of fresh media for further cell concentration reduction. When a desired cell concentration is achieved, new generation of cells is seeded on new cell culture sites 202 by either actively dispensing droplets of the cell suspension from the droplet 242 and translating them to new cell culture sites 202, or by passively dispensing droplets with cells on cell culture sites 202 from the droplet 242 (FIG. 9(f)). The inventors have demonstrated subculturing several generations of mammalian cells in the same DMF device following the procedure outlined above.

Assaying Adherent Cells

The invention also permits assaying adherent cells in droplets in DMF devices. Devices with cells seeded on CCSs 202 are placed in incubators for few hours or overnight to allow cell attachment and adjustment to a DMF environment (FIG. 10(a)). When adhered cells 204 are ready for assaying, droplets of reagents and washing solutions are deposited on cell culture sites 202 either by actively dispensing the droplets (externally or from device reservoirs) and translating them to cell culture sites 202, or by passive dispensing/exchange from source droplets 250 (FIG. 10(b)). Source droplets 250 are either dispensed via DMF from reservoirs or they can be externally deposited on a device. Washing solutions and reagents are delivered to and incubated with cells following cell assay protocols (FIG. 10(c)). Upon assay completion, cell response to a stimulus (e.g. a lead drug compound) can be detected and measured by apparatus 260 which may be any standard means of cell response detection (e.g. fluorescence microscopy, microplate reader to give a few examples) (FIG. 10(d)). Cells can be analyzed either adhered to CCSs or they can be detached from the device surface and analyzed in suspension. The suspension of cells can also be translated to another location in a DMF device for analysis or it can be removed from the device and analyzed externally.

In assays targeting extracellular biochemistry (growth factors, signaling molecules, metabolic products, etc.), cell response to stimulus (i.e. secreted molecules) is detected in droplets 214 of media on cell culture sites 202 where cells are grown and stimulated with reagents. The media droplets can be analyzed on cell culture sites 202, or alternatively, they can be removed from cell culture sites 202 (e.g. by a bigger source droplet) and the signal can be detected on another spot. The contents of media droplets can also be analyzed externally. Droplets of the media may be analyzed by immunoassays or other means.

Multiplexed Adherent Cell Culture/Cell Assays

Referring to FIG. 1, device 100 may be used in multiplexed assays where cells of one kind or multiple kinds are assayed with one or multiple reagents simultaneously in which cell culturing may be involved as well. In addition, single cell culture sites 202 can be seeded with multiple cell lines (cell co-culture). Assay reagents and/or culture media can be delivered to cell culture sites 202 via passive dispensing/exchange or in actively dispensed droplets.

In a multiplexed assay, a single source droplet can deliver reagents to multiple cell culture sites 202 (serial passive dispensing/exchange), or to only one cell culture site 202 (parallel passive dispensing/exchange). Signals from assayed cells or cell media is detected using multiplexed detection instruments such as microplate readers and microarray scanners.

Culturing, Passaging and Assaying Cells in Suspension

In one embodiment of this invention we demonstrate: (1) growing cells in suspension in nanoliter-microliter droplets in DMF devices (in a cell culture incubator), (2) changing media daily, and 3) splitting cells every 2-3 days. Media change involves adding one or more droplets of fresh media to a droplet containing incubated cells in suspension and thereby partially replenishing growth media. Cells are further incubated in the combined droplet or in smaller droplets generated by splitting the combined droplet. Cell subculture or splitting is achieved similarly to media change by combining (merging and mixing) a droplet containing incubated cells and a droplet of fresh media, splitting the combined droplet, and repeating this procedure using the split droplet(s) until a desired cell concentration is reached. Cells in final droplets are then cultured in the same device as a new generation of cells.

Cells in suspension do not require substrate that promotes cell adhesion and, therefore, they can be cultured in droplets anywhere in a DMF device including cell culture sites. However, in a long-term culture, surface occupied by a droplet containing cells becomes fouled and hydrophilic, thus simple DMF operations such as mixing and splitting become challenging. Hence, for efficient media change and cell splitting, passive dispensing/exchange technique has to be employed. Passive exchange enables removing cells with a source droplet (of media) from the culturing area to another non-fouled, hydrophobic location where cells can be split and further resuspended in fresh media. Cells are then seeded in the same device (typically at a new culturing location).

Similarly, assaying cells in suspension can be executed anywhere in a DMF device including cell culture sites. Droplets of assay reagents are merged and mixed with droplets containing cells according to cell assay protocols while cell response to a stimulus is detected and measured. If assays involve long incubation times (e.g., overnight) surface fouling becomes an obstacle in droplet manipulation and passive exchange has to be employed to remove cells from fouled areas and translate them to non-fouled, hydrophobic areas enabling further assay execution.

The use of the digital microfluidics for conducting droplet-based cell assays and cell culture using digital microfluidics will now be illustrated with the following non-limiting examples/studies. This technique has great potential as a simple yet versatile analytical tool for implementing cell-based analysis on the microscale.

Device Design and Fabrication

Digital microfluidic devices were fabricated using conventional microfabrication methods. 100 nm thick gold electrodes were patterned on the bottom plate of a device (glass wafer) and coated with 2 μm of Parylene-C and 50 nm of Teflon-AF. Unpatterned indium-tin oxide (ITO) coated glass substrates were coated with 50 nm of Teflon-AF. Devices were assembled with an unpatterned ITO-glass top plate and a patterned bottom plate and separated by a ~150 μm thick spacer. Driving potentials (100-140 $V_{RMS}$) were generated by amplifying the output of a function generator operating at 15 kHz. Droplets were sandwiched between the two plates and actuated by applying driving potentials between the top reference electrode 22 and sequential electrodes 14 on the bottom plate (FIG. 2(a)) via the exposed contact pads. Basic units of most devices had a basic geometry similar to that shown in FIG. 3 with the addition of reservoirs. Source droplets (~800 mL) were actuated on 2.5 mm×2.5 mm actuation electrodes, and smaller droplets (~100 mL) were actuated on 0.8 mm×0.8 mm actuation electrodes. Devices were sterilized in 70% ethanol prior to use.

Cell Culture

NIH-3T3 cells (mouse fibroblasts) and HeLa cells (human epithelial cells) were maintained in a humidified atmosphere (5% $CO_2$, 37° C.) in Dulbecco's Modified Eagle's Medium (DMEM) supplemented with 10% fetal bovine serum, penicillin (100 IU $mL^{-1}$), and streptomycin (100 μg $mL^{-1}$). Cells were subcultured every 2-3 days at 5×10$^3$ cells $cm^{-2}$. Jurkat T-cells (human leukemia lymphocytes) were maintained in a humidified atmosphere (5% CO2, 37° C.) in RPMI 1640 medium supplemented with 10% fetal bovine serum, penicillin (100 IU $mL^{-1}$), and streptomycin (100 μg $mL^{-1}$). Cells were subcultured every 3-4 days at ~5×10$^5$ cells $mL^{-1}$. Prior to each DMF experiment, all cells were suspended in DMEM with the addition of 0.05% (wt/v) pluronic F68 (Sigma-Aldrich) at ~7×10$^5$-2×10$^6$ cells $mL^{-1}$. Cell number and viability were quantified using a hemocytometer and trypan blue exclusion (Invitrogen Canada) immediately prior to all experiments.

Pluronics are block copolymers formed from poly(propylene oxide) (PPO) and poly(ethylene oxide) (PEO), and are commonly used as surface coatings for preventing non-specific protein adsorption. In our work, we used pluronics in solution, rather than as a surface coating; we hypothesize that in this configuration, the polymer coats cells and proteins in a manner such that their functionality is retained, but adsorption to hydrophobic surfaces is minimized. We note that pluronic F68 has been used extensively in cell-based assays with no evidence for detrimental effects on cell vitality,[19,20] and it is even used as a constituent in commercial cell growth media. Our experiments support this trend—Jurkat T-cells incubated in medium containing 0.2% (wt/vol) F68 for 4 days (humidified incubator, 5% CO2, 37° C.) had identical growth rates and morphology as cells grown in media without pluronics.

DMF Cell Seeding

CCSs were formed by depositing 500 mL droplets of fibronectin (100 μg $mL^{-1}$ in dd$H_2O$) on designated areas in DMF devices. Fibronectin solution was air-dried resulting in ~1 mm$^2$ bio-substrates with ~0.05 μg of fibronectin. Cell suspension in medium was delivered to CCSs by passive dispensing from a source droplet CCS droplets were ~150-200 nL in volume and contained ~140-500 cells. Adherent cells were allowed to attach to the substrate and adapt overnight in a cell culture incubator (5% $CO_2$, 37° C.).

DMF Cell Culture

NIH-3T3 and HeLa cells were maintained on CCSs in cell culture incubators. The medium was changed via passive exchange every 24 hours. Complete DMEM containing 0.05% (wt/v) pluronic F68 was dispensed in ~800 nL droplets and translated over CCSs while replenishing the media. Complete media exchange was accomplished with two consecutive source droplets and cells were returned to the incubator. No cell detachment was observed during passive media exchange.

Jurkat T-cells were cultured either on CCSs or on other, non-CCS areas of DMF devices. The media was replenished every 24 hours by adding a droplet of fresh media to the droplet with cultured cells.

DMF Cell Subculture

Upon reaching ~80% confluency on CCSs, adherent NIH-3T3 and HeLa cell were subcultured following standard protocols adapted to the DMF format. All reagents and media containing 0.05% (wt/v) pluronic F68 were delivered to cells using passive dispensing/exchange from two consecutive source droplets. Cells were first washed with PBS without $Ca^{2+}/Mg^{2+}$ and then supplied and incubated with GIBCO Trypsin-EDTA dissociation agent (0.25% Trypsin, 1 mM EDTA 4Na) for 5-10 min at 37° C. A DMEM source droplet containing serum was then translated to the CCS to block the dissociation agent, whereby harvested cells were resuspended in DMEM at the ~1:4 ratio. The DMEM droplet with suspended cells was actuated away from the CCS and used either as a source droplet or a reservoir droplet to seed a new generation of cells on a new CCS in the same device. Cells were repeatedly grown and subcultured in the same device.

Jurkat T-cells were subcultured every 2-3 days by employing passive exchange. A source droplet of RPMI 1640 media was translated over a culturing area removing the droplet containing cultured cells and resuspending cells in fresh media at the ~1:4 ratio. A source droplet with cells is used to seed a new generation of cells in the same DMF device.

DMF Cell Viability Assay

NIH-3T3 cells cultured on CCSs were assayed for viability via DMF. Source droplets of 0.05% (wt/v) pluronic F68 (Sigma-Aldrich) in phosphate buffered saline containing viability dyes, calcein AM (1 µM) and ethidium homodimer-1 (2 µM) (Invitrogen Canada), were dispensed in a device and translated over CCSs. With two consecutive source droplets, growth media was completely removed from CCSs and replaced with the viability dyes. Cells were incubated with the dyes at room temperature and visualized using stereomicroscope. Viability of cells was generally higher than 95%. In addition, there was no significant difference in morphology between cells grown on CCSs and cells grown in cell culture flasks.

It will be understood that when doing cell culture or cell assays, the suspension of cells may contain a combination of cells, a suspension medium, and a non-ionic surfactant. The suspension medium may be selected to facilitate cell-containing droplet actuation by preventing non-specific adsorption of cells and proteins to device surfaces. The suspension of cells may be a combination of cells and a suspension medium, comprised of block copolymers formed from poly(propylene oxide) and poly(ethylene oxide), pluronic F68, pluronic F127, hydrophilic polymers; sodium bicarbonate, phosphate buffered saline (PBS), HEPES, other biological buffers, and any combination thereof, which may be combined or mixed with cell culture medium which in turn may include balanced salt solutions, nutrient mixtures, basal media, complex media, serum free media, insect cell media, virus production media, serum, fetal bovine serum, serum replacements, antibiotics, antimycotics, and any combination thereof.

In an embodiment, the suspension of cells may be a combination of cells, phosphate buffered saline, and pluronic F68. The droplets including cell assay reagents may include chemicals, biochemicals, drugs, drug lead compounds, toxins, surfactants, transfection reagents, plasmids, supplements, anti-clumping agents, streptavidin, biotin, antibody production enhancers, antibodies, antibody ligands, nucleic acids, nucleic acid binding molecules, enzymes, proteins, viruses, cell process agonists or antagonists; labeling agents, fluorescent dyes, fluorogenic dyes, viability dyes, calcein AM, ethidium homodimer-1, quantum dots, nano particles; block copolymers formed from poly(propylene oxide) and poly(ethylene oxide), pluronic F68, pluronic F127, hydrophilic polymers, sodium bicarbonate, phosphate buffered saline (PBS), HEPES, other biological buffers, and any combination thereof, which may be combined or mixed with a cell culture medium which in turn may include balanced salt solutions, nutrient mixtures, basal media, complex media, serum free media, insect cell media, virus production media, serum, fetal bovine serum, serum replacements, antibiotics, antimycotics, and any combination thereof.

The cells grown in DMF devices may include primary/isolated or transformed/cultured cells selected from the group consisting of various eukaryotic and prokaryotic cells, including animal cells (blood cells, human leukemia cells, lymphocytes, beta cells, oocytes, egg cells, primary cells, primary bone marrow cells, stem cells, neuronal cells, endothelial cells, epithelial cells, fibroblasts), insect cells, plant cells, bacterial cells, archebacterial cells.

As used herein the word "incubation" can mean allowing a reaction to take place over a period of time under specified conditions. For cell assays involving exposing cells to one or more cell assay reagents, the incubation period may be very short or almost instantaneous upon exposure wherein the reaction or response of the cells to the reagent occurs quickly. For cell culture, "incubation" can mean maintaining the cells growing or alive under specific conditions and the period of time of the "incubation" may be arbitrary, after which point the cells may be subcultured, assayed or subject to further culturing.

The results disclosed herein demonstrate the utility of the present invention for its application of digital microfluidics to multiplexed, high throughput, phenotypic cell-based assays, an important tool used in drug discovery and environmental monitoring. To facilitate high-throughput screening, arrays of DMF cell culture sites (FIG. 1) can be addressed with compounds from chemical libraries, and the potential drugs evaluated on the basis of observed phenotypic changes. The proposed method will enable high-throughput phenotypic screening with 100-1000× lower reagent consumption than conventional methods; in addition, the devices are inexpensive (relative to robotic dispensers), and have small laboratory footprint and no moving parts. This method could transform high-throughput screening, making it attractive to pharmaceutical companies and accessible for basic and applied scientists, world-wide.

In addition to cell assaying, the inventors disclose herein the first multigenerational lab-on-a-chip cell culture using DMF devices. Cells are repeatedly seeded, grown and subcultured in nanoliter volumes yielding a multigenerational cell culture in a same DMF device. DMF devices are easily automated and as such have a high potential to be used as tool for a completely automated microscale cell culture system.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES (1) Verkman, A. S., "Drug discovery in academia," *American Journal of Physiology-Cell Physiology* 2004, 286, C465-C474.
(2) El-Ali, J., Sorger, P. K., Jensen, K. F., "Cells on chips," *Nature* 2006, 442, 403-411.
(3) Unger, M. A., Chou, H. P., Thorsen, T., Scherer, A., Quake, S. R., "Monolithic Microfabricated Valves and Pumps by Multilayer Soft Lithography," *Science* 2000, 288, 113-116.
(4) Yu, H. M., Alexander, C. M., Beebe, D. J., "A plate reader-compatible microchannel array for cell biology assays," *Lab on a Chip* 2007, 7, 388-391.
(5) Le Pesant, J.-P., 1987, U.S. Pat. No. 4,636,785.
(6) Ohkawa, T., 1996, U.S. Pat. No. 5,486,337.
(7) Washizu, M., Kurosawa, O., 1998, Japan 10267801.
(8) Washizu, M., "Electrostatic Actuation of Liquid Droplets for Microreactor Applications," *IEEE Transactions on Industry Applications* 1998, 34, 732-737.
(9) Lee, J., Moon, H., Fowler, J., Schoellhammer, T., Kim, C.-J., "Electrowetting and electrowetting-on-dielectric for microscale liquid handling," *Sensors & Actuators A* 2002, 95, 259-268.
(10) Pollack, M. G., Fair, R. B., Shenderov, A. D., "Electrowetting-based actuation of liquid droplets for microfluidic applications," *Applied Physics Letters* 2000, 77, 1725-1726.
(11) Shenderov, A. D., 2003, U.S. Pat. No. 6,565,727.
(12) Shenderov, A. D., 2007, U.S. Pat. No. 7,255,780.
(13) Elrod, S. A., Peeters, E. T., Biegelsen, D. K., Dunec, J. L., 2006, U.S. Pat. No. 7,147,763.
(14) Pamula, V. K., Pollack, M. G., Paik, P., H., R., Fair, R., 2005, U.S. Pat. No. 6,911,132.
(15) Chen, T.-H., Su, C.-M., Shih, H.-C., Yang, C.-T., "*Selective Wettability Assisted Nanoliter Sample Generation via Electrowetting-Based Transportation*," Proceedings of the Fifth International Conference on Nanochannels, Microchannels and Minichannels (ICNMM2007), Puebla, Mexico, Jun. 18-20 2007.
(16) Pollack, M., G., Pamula, V., K., Srinivasan, V., Paik, P., Y., Eckhardt, A., E., Fair, R., B., 2007 WO/2007/120241.
(17) Huh, N., Lee, J.-g., 2007, US 20070148763
(18) Fan, S.-K., Huang, P.-W., Wang, T.-T., Peng, Y.-H., "Cross-scale electric manipulations of cells and droplets by frequency-modulated dielectrophoresis and electrowetting," *Lab on a Chip* 2008, 10.1039/b803204a.
(19) Smith, C. M., Hebbel, R. P., Tukey, D. P., Clawson, C. C., White, J. G., Vercellotti, G. M., "Pluronic F-68 Reduces the Endothelial Adherence and Improves the Rheology of Liganded Sickle Erythrocytes," *Blood* 1987, 69, 1631-1636.
(20) Mizrahi, A., "Pluronic Polyols in Human Lymphocyte Cell Line Cultures," *Journal of Clinical Microbiology* 1975, 2, 11-13.

Therefore what is claimed is:

1. A digital microfluidic device for conducting cell assays and cell culture, comprising:
    a first substrate;
    a first array of discrete electrodes formed on said first substrate;
    at least one first coating covering each discrete electrode, such that said discrete electrodes are electrically insulated from one another, and wherein an outer surface of said at least one first coating forms a first hydrophobic working surface;
    a second substrate;
    at least one second coating covering the second substrate, wherein an outer surface of the at least one second coating forms a second hydrophobic working surface;
    at least one reference electrode provided on said first substrate or said second substrate;
    wherein said second substrate is provided in a spaced relationship relative to said first substrate, thus defining a space between said first substrate and said second substrate capable of contacting a cell-containing liquid droplet between said first hydrophobic working surface and said second hydrophobic working surfaces;
    wherein said discrete electrodes and said reference electrode are connectable to an electrode controller, such that said discrete electrodes and said reference electrode may be activated to translate the cell-containing liquid droplet; and
    wherein one or both of said first hydrophobic working surface and said second second hydrophobic working surface includes at least one locally modified hydrophilic hydrophilic region, such that within said locally modified hydrophilic region, said one or both of said first hydrophobic working surface and said second hydrophobic working surface is configured for cell attachment and cell culture, and wherein said discrete electrodes and said reference electrode may be activated to selectively contact the cell-containing liquid droplet with said locally modified hydrophilic region for attachment of cells from the cell-containing liquid droplet to said locally modified hydrophilic region for subsequent cell culture.

2. The device according to claim 1 wherein at least one locally modified region comprises a bio-substrate provided thereon.

3. The device according to claim 2 wherein at least one locally modified region has a bio-substrate that includes cell specific constituents.

4. The device according to claim 3 wherein said cell specific constituents are extracellular matrix proteins.

5. The device according to claim 4 wherein said extracellular matrix proteins include any one of fibronectin, laminin, collagen, elastin and any combination thereof.

6. The device according to claim 3 wherein said cell specific constituents are synthetic molecules comprised of one of poly-L-lysine, poly-D-lysine and any combination thereof.

7. The device according to claim 3 wherein said cell specific constituents include other cells.

8. The device according to claim 7 wherein said other cells include feeder layer cells.

9. The device according to claim 2 wherein at least one locally modified region contains attached/immobilized affinity assay agents including antibodies.

10. The device according to claim 2 wherein at least one locally modified region includes a layer of adherent cells adhered thereto.

11. The device according to claim 2 wherein an area of at least one locally modified region is between approximately one quarter and one ninth of the area of a neighbouring discrete electrode.

12. The device according to claim 2 wherein at least one locally modified region is located over a discrete electrode.

13. The device according to claim 2 wherein at least one locally modified region is located over a portion of two or more discrete electrodes.

14. The device according to claim 2 wherein at least one locally modified region is located over a region of said first substrate that does not include an electrode.

15. The device according to claim 1 wherein at least one locally modified region comprises a region with a modified surface chemistry.

16. The device according to claim 15 wherein said region with a modified surface chemistry is formed by plasma treatment.

17. The device according to claim 15 wherein at least one locally modified region contains attached/immobilized affinity assay agents including antibodies.

18. The device according to claim 15 wherein at least one locally modified region includes a layer of adherent cells adhered thereto.

19. The device according to claim 15 wherein an area of at least one locally modified region is between approximately one quarter and one ninth of the area of a neighbouring discrete electrode.

20. The device according to claim 15 wherein at least one locally modified region is located over a discrete electrode.

21. The device according to claim 15 wherein at least one locally modified region is located over a portion of two or more discrete electrodes.

22. The device according to claim 15 wherein at least one locally modified region is located over a region of said first substrate that does not include an electrode.

23. The device according to claim 15 wherein said one or more locally modified hydrophilic regions are located only on the first hydrophobic working surface.

24. The device according to claim 15 wherein said one or more locally modified hydrophilic regions are located only on said second hydrophobic working surface.

25. The device according to claim 15 wherein said one or more locally modified hydrophilic regions is a plurality of modified regions located on both the first and second hydrophobic working surfaces.

26. The device according to claim 15 including a detection and analyzing device for detecting and analyzing cells, signals from cells and/or reaction products formed between cells and cell assay reagents on said first and/or second working surfaces.

27. The device according to claim 26 wherein said detection and analyzing device is selected from the group consisting of optical sensors, optical detectors comprising a light source and a photodetector, optical detectors that measure absorbance, fluorescence, epifluorescence, chemiluminescence, UV light detector, radiometric detector, scanning, imaging, and confocal microscopy detectors, CCD cameras, and microplate readers, microarray scanners, surface plasmon resonance detectors, electrochemical detectors by amperometry, voltammetry, or conductivity measurements, acoustic sensors by piezoelectrics.

28. The device according to claim 15 wherein said at least one locally modified hydrophilic region is a site to which adherent cells can adhere.

29. The device according to claim 15 wherein said first substrate surface includes a dielectric coating, and wherein said first hydrophobic working surface is a surface of the dielectric coating and wherein the surface of the dielectric coating is hydrophobic.

30. The device according to claim 15 wherein said first substrate includes a dielectric layer and a hydrophobic coating on a surface of said dielectric layer, and wherein said first hydrophobic working surface is a surface of the hydrophobic coating.

31. The device according to claim 15 wherein said second substrate is substantially transparent.

32. The device according to claim 2 including a control means connectable to the electrode controller and being programmed to translate liquid droplets of cell suspensions, liquid droplets of cell assay reagents, and liquid droplets of cell culture reagents across said array of discrete electrodes between said first hydrophobic working surface and said second hydrophobic working surface in a selected order defined by a selected cell assay protocol or cell culture protocol for which said control means is programmed.

33. The device according to claim 2 wherein said one or more locally modified hydrophilic regions are located only on the first hydrophobic working surface.

34. The device according to claim 2 wherein said one or more locally modified hydrophilic regions are located only on said second hydrophobic working surface.

35. The device according to claim 2 wherein said one or more locally modified hydrophilic regions is a plurality of modified regions located on both the first and second hydrophobic working surfaces.

36. The device according to claim 2 including one or more cell sample reservoirs in flow communication with the first and second hydrophobic working surfaces for holding at least one suspension of cells, and including one or more reagent reservoirs in flow communication with said first hydrophobic working surface and said second hydrophobic working surface for holding one or more cell assay reagents, and one or more cell culture reagents.

37. The device according to claim 36 including dispensing means coupled to said one or more cell sample reservoirs and coupled to said one or more reagent reservoirs for dispensing liquid droplets of said at least one suspension of cells, liquid droplets of said one or more cell assay reagents, and liquid droplets of said cell culture reagents onto said first and second hydrophobic working surfaces.

38. The device according to claim 2 wherein said first substrate surface includes a dielectric coating, and wherein said first hydrophobic working surface is a surface of the dielectric coating and wherein the surface of the dielectric coating is hydrophobic.

39. The device according to claim 2 wherein said first substrate includes a dielectric layer and a hydrophobic coating on a surface of said dielectric layer, and wherein said first hydrophobic working surface is a surface of the hydrophobic coating.

40. The device according to claim 39 including a second electrode array of discrete electrodes located between the dielectric layer and said hydrophobic coating.

41. The device according to claim 39 wherein said reference electrode includes a reference electrode array provided between the dielectric layer and the hydrophobic coating, wherein the reference electrode array is electrically insulated from the discrete electrodes.

42. The device according to claim 2 wherein said second substrate surface includes a dielectric coating.

43. The device according to claim 2 wherein said at least one reference electrode is located on the first substrate and electrically insulated from the discrete electrodes.

44. The device according to claim 2, including a second array of discrete electrodes located between the surface of the second substrate and said second working surface of said second substrate.

45. The device according to claim 2 wherein said at least one reference electrode is provided on said second substrate.

46. The device according to claim 2 wherein said at least one reference electrode is an array of reference electrodes interleaved with said first array of discrete electrodes on said first substrate such that each of said reference electrodes is proximal to one or more corresponding discrete electrodes.

47. The device according to claim 2 wherein said second substrate is substantially transparent.

48. The device according to claim 2 including a detection and analyzing device for detecting and analyzing cells, signals from cells and/or reaction products formed between cells and cell assay reagents on said first and/or second working surfaces.

49. The device according to claim 48 wherein said detection and analyzing device is selected from the group consisting of optical sensors, optical detectors comprising a light source and a photodetector, optical detectors that measure absorbance, fluorescence, epifluorescence, chemiluminescence, UV light detector, radiometric detector, scanning, imaging, and confocal microscopy detectors, CCD cameras, and microplate readers, microarray scanners, surface plasmon resonance detectors, electrochemical detectors by amperometry, voltammetry, or conductivity measurements, acoustic sensors by piezoelectrics.

50. The device according to claim 2 wherein said at least one locally modified hydrophilic region is a site to which adherent cells can adhere.

51. A digital microfluidic based method of performing any one or both of cell assays and cell culture, comprising the steps of:
   a) providing a digital microfluidic device according to claim 1;
   b) dispensing one or more first liquid droplets containing a suspension of at least one kind of cells in a cell medium onto one or more first positions on the digital microfluidic device, and optionally dispensing one or more second liquid droplets containing cell assay/cell culture reagents onto one or more second positions on the digital microfluidic device;
   c) translating at least the one or more first liquid droplets to at least one locally modified hydrophilic region, and optionally translating at least the one or more second liquid droplets to said at least one locally modified hydrophilic region;
   d) incubating the cells at each locally modified hydrophilic region in an incubation medium contained either in said first liquid droplets or in said second liquid droplets or in a mixture thereof; and
   e) analyzing the at least one locally modified hydrophilic region to characterize one or both of the cells and cell medium in each locally modified hydrophilic region.

52. The method according to claim 51 where step b) of dispensing and step c) of translating first and optionally second droplets includes dispensing of first and optionally second droplets by external means directly on the at least one locally modified hydrophilic region.

53. The method according to claim 51 including at least one additional liquid droplet dispensing step of dispensing one or more of said second liquid droplets and mixing and incubating said one or more second liquid droplets with corresponding said one or more first liquid droplets prior to step c), and wherein said step c) of translating at least the one or more first liquid droplets to said at least one locally modified hydrophilic region includes translating the mixture of each of said first and second liquid droplets to a corresponding locally modified hydrophilic region.

54. The method according to claim 51, wherein either after step c), or d), including a second droplet dispensing step of dispensing said one or more second droplets and then translating the one or more second droplets to a corresponding locally modified hydrophilic region, to mix with, or replace, an existing droplet at each locally modified hydrophilic region and thereafter incubate with cells.

55. The method according to claim 51, wherein said second droplet dispensing step is repeated a desired number of times.

56. The method according to claim 51 wherein said locally modified hydrophilic regions are sites to which adherent cells can adhere and wherein incubating step d) includes allowing cells to adhere to each of said at least one locally modified hydrophilic region.

57. The method according to claim 51 wherein said one or more pre-selected positions are modified by depositing a bio-substrate thereon.

58. The method according to claim 57 wherein said bio-substrate is deposited using any one of microprinting, microstamping and photolithography methods.

59. The method according to claim 57 wherein said bio-substrate is produced from cell specific constituents.

60. The method according to claim 59 wherein said cell specific constituents are extracellular matrix proteins.

61. The method according to claim 60 wherein said extracellular matrix proteins include any one of fibronectin, laminin, collagen, elastin and any combination thereof.

62. The method according to claim 59 wherein said cell specific constituents are synthetic molecules comprised of one of poly-L-lysine, poly-D-lysine and any combination thereof.

63. The method according to claim 59 wherein said cell specific constituents are other cells including feeder layer cells.

64. The method according to claim 51 wherein said at least one locally modified hydrophilic region is produced using any one or combination of surface chemistry modification, plasma treatment, hydrophobic layer removal, dielectric layer etching, electrode etching and stamping.

65. The method according to claim 51 wherein said at least one locally modified hydrophilic region contains attached/immobilized affinity assay agents including antibodies.

66. The method according to claim 51 wherein said one or more first droplets each contain a single cell.

67. The method according to claim 51 wherein in step e) said one or more droplets from one or more locally modified hydrophilic regions are translated to one or more selected positions on said digital microfluidic device for analysis or the said one or more droplets from one or more locally modified hydrophilic regions are removed from the digital microfluidic device and analyzed externally.

68. The method according to claim 51 wherein in step e) of analyzing said one or more locally modified hydrophilic regions or analyzing one or more droplets removed from the locally modified hydrophilic regions is performed by detecting signals emitted from the locally modified hydrophilic regions or the said droplets using a device selected from the group consisting of optical sensors, optical detectors comprising a light source and a photodetector, optical detectors that measure any one or combination of absorbance, fluorescence, epifluorescence, and chemiluminescence, UV light detectors, radiometric detectors, any one of scanning, imaging, and confocal microscopy detectors, CCD cameras, microplate readers, microarray scanners, surface plasmon resonance detectors, electrochemical detectors by amperometry, voltammetry, or conductivity measurements, acoustic sensors by piezoelectrics.

69. The method according to claim 51 wherein any one or combination of said one or more first and optionally said one or more second droplets is split into at least two smaller droplets during any step of the method.

70. The method according to claim 51 wherein said cell medium for said cell suspension is selected to facilitate cell-containing droplet actuation by preventing non-specific adsorption of cells and proteins to one or both of of said first hydrophobic working surface and said second hydrophobic working surface.

71. The method according to claim 51 wherein after incubating the cells on one or more locally modified hydrophilic regions in step d), including translating one or more droplets containing a cell washing solution to said one or more locally modified hydrophilic regions to replace the incubation medium and wash adhered cells from the incubation medium, then translating one or more droplets containing a cell dissociation agent to said one or more locally modified hydrophilic regions, and incubating with adhered cells in order to detach the cells adhered to said one or more locally modified hydrophilic regions, then mixing one or more droplets containing the dissociation agent and said detached adhered cells with one or more droplets containing any one of at least one dissociation-blocking agent, a biological reagent, a chemical reagent, a biochemical reagent, and any combination thereof, wherein a biological reagent can be cell culture media, thereby forming a secondary droplet with re-suspended cells, and wherein said re-suspended cells can be optionally further assayed or cultured.

72. The method according to claim 71 including mixing said secondary droplet with re-suspended cells or any droplet split therefrom with one or more droplets containing cell culture media and translating at least some cells suspended in the cell culture media to at least one new locally modified hydrophilic region to seed a new generation of cells.

73. The method according to claim 51 wherein after incubating the cells in suspension on locally modified hydrophilic regions in step d), including translating one or more droplets containing a cell culture reagents and/or cell assay reagents to said one or more locally modified hydrophilic regions to remove cells from said one or more locally modified hydrophilic regions, thereby forming a secondary droplet with re-suspended cells, and wherein said re-suspended cells can be optionally further assayed or cultured.

74. The method according to claim 51 wherein one or both of said first hydrophobic working surface and said second hydrophobic working surface includes one or more hydrophilic areas and including translating a primary droplet over said one or more hydrophilic areas, said primary droplet having a base area larger than said one or more hydrophilic areas whereby a first smaller droplet is removed from said primary droplet and remains behind on said one or more hydrophilic areas, and wherein said primary droplet is any one of said one or more first droplets, second droplets and combinations of the first and the second droplets.

75. The method according to claim 72 including translating additional one or more primary droplets over said one or more hydrophilic areas already containing a said first smaller droplet, whereby the first smaller droplet is replaced by a second smaller droplet removed from said additional primary droplet.

76. The method according to claim 51 conducted in a substantially sterile chamber.

77. The method according to claim 76 including controlling and regulating conditions in the sterile chamber including humidity, temperature and atmosphere.

* * * * *